United States Patent
Qian et al.

(10) Patent No.: US 8,349,856 B2
(45) Date of Patent: *Jan. 8, 2013

(54) QUINAZOLINE BASED EGFR INHIBITORS

(75) Inventors: Changgeng Qian, Wayland, MA (US);
Xiong Cai, Belmont, MA (US)

(73) Assignee: Curis, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/155,788

(22) Filed: Jun. 8, 2011

(65) Prior Publication Data

US 2011/0295004 A1   Dec. 1, 2011

Related U.S. Application Data

(63) Continuation of application No. 11/852,474, filed on Sep. 10, 2007, now Pat. No. 7,977,347.

(60) Provisional application No. 60/843,644, filed on Sep. 11, 2006, provisional application No. 60/895,873, filed on Mar. 20, 2007.

(51) Int. Cl.
*A61K 31/517* (2006.01)
(52) U.S. Cl. ...................... 514/266.4; 544/293
(58) Field of Classification Search ............ 514/266.4; 544/293
See application file for complete search history.

(56) References Cited

U.S. PATENT DOCUMENTS 6,414,148 B1 *   7/2002   Thomas et al. ............... 544/283

* cited by examiner

*Primary Examiner* — Douglas M Willis
(74) *Attorney, Agent, or Firm* — Elmore Patent Law Group, P.C.; Edgar W. Harlan; Carolyn S. Elmore, Esq.

(57) ABSTRACT

The present invention relates to quinazoline containing zinc-binding moiety based derivatives of formula I that have enhanced and unexpected properties as inhibitors of epidermal growth factor receptor tyrosine kinase (EGFR-TK) and their use in the treatment of EGFR-TK related diseases and disorders such as cancer.

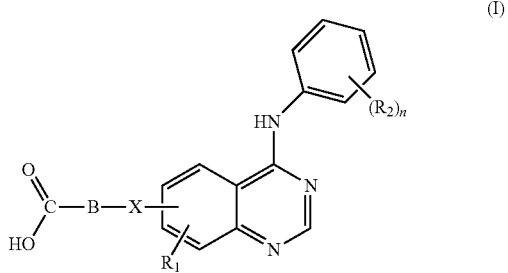

19 Claims, No Drawings

QUINAZOLINE BASED EGFR INHIBITORS

RELATED APPLICATIONS SECTION

This application is a continuation of U.S. application Ser. No. 11/852,474 filed on Sep. 10, 2007, which claims the benefit of U.S. application No. 60/843,644 filed on Sep. 11, 2006 and U.S. application No. 60/895,873 filed on Mar. 20, 2007. The entire teachings of the above applications are incorporated herein by reference.

BACKGROUND OF THE INVENTION

The epidermal growth factor receptor (EGFR, Erb-B1) belongs to a family of proteins, involved in the proliferation of normal and malignant cells (Artega, C. L., *J. Clin Oncol* 19, 2001, 32-40). Overexpression of Epidermal Growth Factor Receptor (EGFR) is present in at least 70% of human cancers (Seymour, L. K., *Curr Drug Targets* 2, 2001, 117-133) such as, non-small cell lung carcinomas (NSCLC), breast cancers, gliomas, squamous cell carcinoma of the head and neck, and prostate cancer (Raymond et al., *Drugs* 60 Suppl 1, 2000, discussion 41-2; Salomon et al., *Crit. Rev Oncol Hematol* 19, 1995, 183-232; Voldborg et al., *Ann Oncol* 8, 1997, 1197-1206). The EGFR-TK is therefore widely recognized as an attractive target for the design and development of compounds that can specifically bind and inhibit the tyrosine kinase activity and its signal transduction pathway in cancer cells, and thus can serve as either diagnostic or therapeutic agents. For example, the EGFR tyrosine kinase (EGFR-TK) reversible inhibitor, TARCEVA®, is recently approved by the FDA for treatment of NSCLC and advanced pancreatic cancer. Other anti-EGFR targeted molecules have also been approved such as IRESSA®.

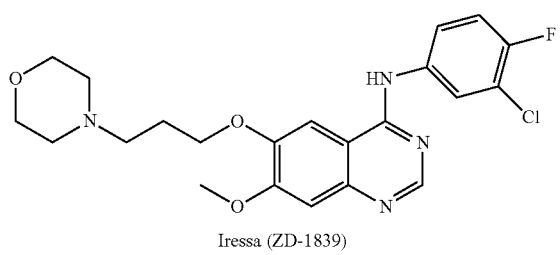

Iressa (ZD-1839)

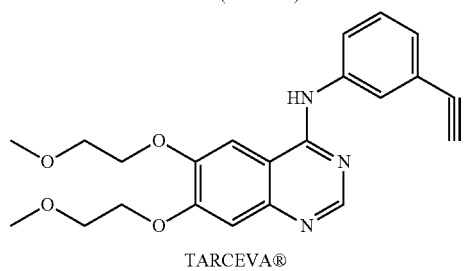

TARCEVA®

Despite the early success of Tarceva, it has become clear that selectively targeting individual kinases can lead to the development of drug resistant tumors. Cells that have developed mutations within the drug/kinase binding pocket display a growth advantage in the presence of drug eventually leading to disease progression. Accordingly, the discovery and development of new molecules to target such kinases may be important to treat patients that have already developed resistance to current therapeutic molecules.

SUMMARY OF THE INVENTION

The present invention relates to certain quinazolines that inhibit one or more epidermal growth factor receptor tyrosine kinase (EGFR-TK), HDAC or matrix metalloproteinase (MMP) and/or HER2 and are effective for treating diseases related to EGFR-TK activity, HDAC activity and/or HER2 activity, such as cancer and proliferative diseases.

Accordingly, the present invention provides a compound having the general Formula I:

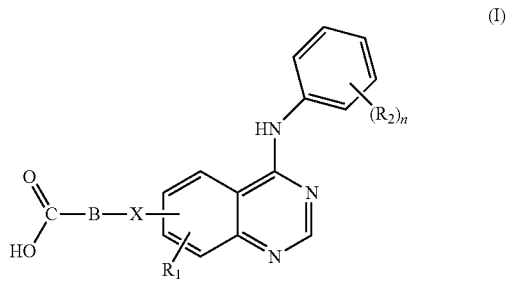

(I)

or its geometric isomers, enantiomers, diastereomers, racemates, pharmaceutically acceptable salts, prodrugs (e.g., esters) and solvates thereof, wherein X is O, S, $CH_2$, or —CONH—, preferably O;

B is an unsubstituted or hydroxy substituted $C_3$ to $C_9$ alkylene, preferably an unsubstituted or hydroxy substituted straight chain $C_5$ to $C_7$ alkylene, an unsubstituted or hydroxy substituted most preferably a straight chain $C_4$ or $C_6$ alkylene, wherein B can be a β-hydroxy alkylene;

$R_1$ is independently selected from hydrogen; hydroxy, $C_1$ to $C_4$ alkoxy, preferably methoxy; or substituted $C_1$ to $C_4$ alkoxy, preferably $C_1$ to $C_4$ alkoxy substituted $C_1$ to $C_4$ alkoxy, such as most preferably methoxyethoxy; and $R_2$ is each independently selected from halogen (preferably Br, Cl and F), hydroxy, $C_1$ to $C_4$ alkyl, $C_2$ to $C_4$ alkenyl, and $C_2$ to $C_4$ alkynyl (preferably ethynyl);

n is 1, 2 or 3, preferably 1 or 2.

DETAILED DESCRIPTION OF THE INVENTION

In a first embodiment of the compounds of the present invention are compounds represented by formula (I) as illustrated above, or its geometric isomers, enantiomers, diastereomers, racemates, pharmaceutically acceptable salts, prodrugs and solvates thereof.

In a second embodiment of the compounds of the present invention are compounds represented by formula (II) as illustrated below, or its geometric isomers, enantiomers, diastereomers, racemates, pharmaceutically acceptable salts, prodrugs and solvates thereof:

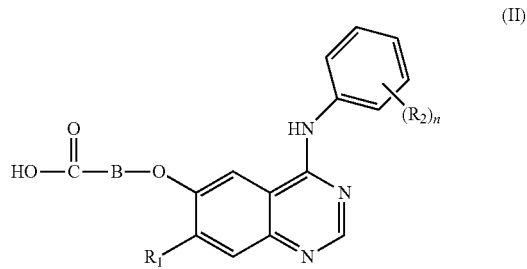

(II)

wherein B, $R_1$, $R_2$, and n are as previously defined.

In a third embodiment of the compounds of the present invention are compounds represented by formula (III) as illustrated below, or its geometric isomers, enantiomers, diastereomers, racemates, pharmaceutically acceptable salts, prodrugs and solvates thereof:

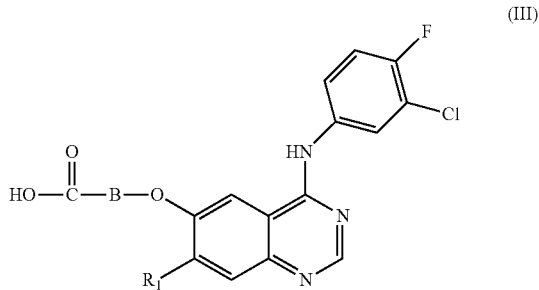

wherein B and $R_1$ are as previously defined.

In a particularly preferred embodiment, the compound has the Formula III wherein $R_1$ is a methoxy and B is an unsubstituted or hydroxy substituted straight chain $C_6$ alkylene and pharmaceutically acceptable salts and prodrugs (e.g. esters) thereof.

In a fourth embodiment of the compounds of the present invention are compounds represented by formula (IV) as illustrated below, or its geometric isomers, enantiomers, diastereomers, racemates, pharmaceutically acceptable salts, prodrugs and solvates thereof:

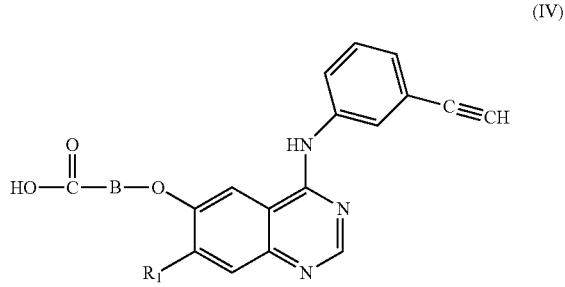

wherein B and $R_1$ are as previously defined.

In a fifth embodiment of the compounds of the present invention are compounds represented by formula (V) as illustrated below, or its geometric isomers, enantiomers, diastereomers, racemates, pharmaceutically acceptable salts, prodrugs and solvates thereof:

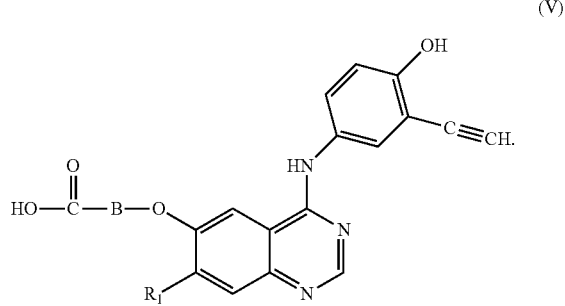

In each of the above embodiments, $R_1$ is preferably hydrogen, hydroxy or methoxy and, independently or collectively, B is preferably an unsubstituted or hydroxy substituted straight chain $C_5$ to $C_7$ alkylene, most preferably a straight chain $C_6$ alkylene.

In a particularly preferred embodiment, the compound has the Formula IV wherein $R_1$ is a methoxy and B is an unsubstituted or hydroxy substituted straight chain $C_6$ alkylene and pharmaceutically acceptable salts and prodrugs (e.g. esters) thereof.

The compounds according to the invention are metabolites of compounds described and claimed in the priority applications of this application and in related application U.S. application Ser. No. 11/852,604, the contents of which are incorporated herein by reference.

The invention further provides methods for the prevention or treatment of diseases or conditions involving aberrant proliferation, differentiation or survival of cells. In one embodiment, the invention further provides for the use of one or more compounds of the invention in the manufacture of a medicament for halting or decreasing diseases involving aberrant proliferation, differentiation, or survival of cells. In preferred embodiments, the disease is cancer. In one embodiment, the invention relates to a method of treating cancer in a subject in need of treatment comprising administering to said subject a therapeutically effective amount of a compound of the invention.

The term "cancer" refers to any cancer caused by the proliferation of malignant neoplastic cells, such as tumors, neoplasms, carcinomas, sarcomas, leukemias, lymphomas and the like. For example, cancers include, but are not limited to, mesothelioma, leukemias and lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), B-cell lymphoma, acute nonlymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma. Further examples include myelodisplastic syndrome, childhood solid tumors such as brain tumors, neuroblastoma, retinoblastoma, Wilms' tumor, bone tumors, and soft-tissue sarcomas, common solid tumors of adults such as head and neck cancers (e.g., oral, laryngeal, nasopharyngeal and esophageal), genitourinary cancers (e.g., prostate, bladder, renal, uterine, ovarian, testicular), lung cancer (e.g., small-cell and non small cell), breast cancer, pancreatic cancer, melanoma and other skin cancers, stomach cancer, brain tumors, tumors related to Gorlin's syndrome (e.g., medulloblastoma, meningioma, etc.), and liver cancer. Additional exemplary forms of cancer which may be treated by the subject compounds include, but are not limited to, cancer of skeletal or smooth muscle, stomach cancer, cancer of the small intestine, rectum carcinoma, cancer of the salivary gland, endometrial cancer, adrenal cancer, anal cancer, rectal cancer, parathyroid cancer, and pituitary cancer.

Additional cancers that the compounds described herein may be useful in preventing, treating and studying are, for example, colon carcinoma, familiary adenomatous polyposis carcinoma and hereditary non-polyposis colorectal cancer, or melanoma. Further, cancers include, but are not limited to, labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma, renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma. In one aspect of the invention, the present invention provides for the use of one or more compounds of the invention in the manufacture of a medicament for the treatment of cancer.

In one embodiment, the present invention includes the use of one or more compounds of the invention in the manufacture of a medicament that prevents further aberrant proliferation, differentiation, or survival of cells. For example, compounds of the invention may be useful in preventing tumors from increasing in size or from reaching a metastatic state. The subject compounds may be administered to halt the progression or advancement of cancer or to induce tumor apoptosis or to inhibit tumor angiogenesis. In addition, the instant invention includes use of the subject compounds to prevent a recurrence of cancer.

This invention further embraces the treatment or prevention of cell proliferative disorders such as hyperplasias, dysplasias and pre-cancerous lesions. Dysplasia is the earliest form of pre-cancerous lesion recognizable in a biopsy by a pathologist. The subject compounds may be administered for the purpose of preventing said hyperplasias, dysplasias or pre-cancerous lesions from continuing to expand or from becoming cancerous. Examples of pre-cancerous lesions may occur in skin, esophageal tissue, breast and cervical intra-epithelial tissue.

"Combination therapy" includes the administration of the subject compounds in further combination with other biologically active ingredients (such as, but not limited to, a second and different antineoplastic agent) and non-drug therapies (such as, but not limited to, surgery or radiation treatment). For instance, the compounds of the invention can be used in combination with other pharmaceutically active compounds, preferably compounds that are able to enhance the effect of the compounds of the invention. The compounds of the invention can be administered simultaneously (as a single preparation or separate preparation) or sequentially to the other drug therapy. In general, a combination therapy envisions administration of two or more drugs during a single cycle or course of therapy.

In one aspect of the invention, the subject compounds may be administered in combination with one or more separate agents that modulate protein kinases involved in various disease states. Examples of such kinases may include, but are not limited to: serine/threonine specific kinases, receptor tyrosine specific kinases and non-receptor tyrosine specific kinases. Serine/threonine kinases include mitogen activated protein kinases (MAPK), meiosis specific kinase (MEK), RAF and aurora kinase. Examples of receptor kinase families include epidermal growth factor receptor (EGFR) (e.g. HER2/neu, HER3, HER4, ErbB, ErbB2, ErbB3, ErbB4, Xmrk, DER, Let23); fibroblast growth factor (FGF) receptor (e.g. FGF-R1, GFF-R2/BEK/CEK3, FGF-R3/CEK2, FGF-R4/TKF, KGF-R); hepatocyte growth/scatter factor receptor (HGFR) (e.g, MET, RON, SEA, SEX); insulin receptor (e.g. IGFI-R); Eph (e.g. CEK5, CEK8, EBK, ECK, EEK, EHK-1, EHK-2, ELK, EPH, ERK, HEK, MDK2, MDK5, SEK); Axl (e.g. Mer/Nyk, Rse); RET; and platelet-derived growth factor receptor (PDGFR) (e.g. PDGFα-R, PDGFβ-R, CSF1-R/FMS, SCF-R/C-KIT, VEGF-R/FLT, NEK/FLK1, FLT3/FLK2/STK-1). Non-receptor tyrosine kinase families include, but are not limited to, BCR-ABL (e.g. p43$^{abl}$, ARG); BTK (e.g. ITK/EMT, TEC); CSK, FAK, FPS, JAK, SRC, BMX, FER, CDK and SYK.

In another aspect of the invention, the subject compounds may be administered in combination with one or more separate agents that modulate non-kinase biological targets or processes. Such targets include histone deacetylases (HDAC), DNA methyltransferase (DNMT), heat shock proteins (e.g. HSP90), and proteosomes.

In a preferred embodiment, subject compounds may be combined with antineoplastic agents (e.g. small molecules, monoclonal antibodies, antisense RNA, and fusion proteins) that inhibit one or more biological targets such as Zolinza, Tarceva, Iressa, Tykerb, Gleevec, Sutent, Sprycel, Nexavar, Sorafinib, CNF2024, RG108, BMS387032, Affinitak, Avastin, Herceptin, Erbitux, AG24322, PD325901, ZD6474, PD184322, Obatodax, ABT737 and AEE788. Such combinations may enhance therapeutic efficacy over efficacy achieved by any of the agents alone and may prevent or delay the appearance of resistant mutational variants.

In certain preferred embodiments, the compounds of the invention are administered in combination with a chemotherapeutic agent. Chemotherapeutic agents encompass a wide range of therapeutic treatments in the field of oncology. These agents are administered at various stages of the disease for the purposes of shrinking tumors, destroying remaining cancer cells left over after surgery, inducing remission, maintaining remission and/or alleviating symptoms relating to the cancer or its treatment. Examples of such agents include, but are not limited to, alkylating agents such as mustard gas derivatives (Mechlorethamine, cylophosphamide, chlorambucil, melphalan, ifosfamide), ethylenimines (thiotepa, hexamethylmelanine), Alkylsulfonates (Busulfan), Hydrazines and Triazines (Altretamine, Procarbazine, Dacarbazine and Temozolomide), Nitrosoureas (Carmustine, Lomustine and Streptozocin), Ifosfamide and metal salts (Carboplatin, Cisplatin, and Oxaliplatin); plant alkaloids such as Podophyllotoxins (Etoposide and Tenisopide), Taxanes (Paclitaxel and Docetaxel), Vinca alkaloids (Vincristine, Vinblastine, Vindesine and Vinorelbine), and Camptothecan analogs (Irinotecan and Topotecan); anti-tumor antibiotics such as Chromomycins (Dactinomycin and Plicamycin), Anthracyclines (Doxorubicin, Daunorubicin, Epirubicin, Mitoxantrone, Valrubicin and Idarubicin), and miscellaneous antibiotics such as Mitomycin, Actinomycin and Bleomycin; anti-metabolites such as folic acid antagonists (Methotrexate, Pemetrexed, Raltitrexed, Aminopterin), pyrimidine antagonists (5-Fluorouracil, Floxuridine, Cytarabine, Capecitabine, and Gemcitabine), purine antagonists (6-Mercaptopurine and 6-Thioguanine) and adenosine deaminase inhibitors (Cladribine, Fludarabine, Mercaptopurine, Clofarabine, Thioguanine, Nelarabine and Pentostatin); topoisomerase inhibitors such as topoisomerase I inhibitors (Ironotecan, topotecan) and topoisomerase II inhibitors (Amsacrine, etoposide, etoposide phosphate, teniposide); monoclonal antibodies (Alemtuzumab, Gemtuzumab ozogamicin, Rituximab, Trastuzumab, Ibritumomab Tioxetan, Cetuximab, Panitumumab, Tositumomab, Bevacizumab); and miscellaneous anti-neoplastics such as ribonucleotide reductase inhibitors (Hydroxyurea); adrenocortical steroid inhibitor (Mitotane); enzymes (Asparaginase and Pegaspargase); anti-microtubule agents (Estramustine); and retinoids (Bexarotene, Isotretinoin, Tretinoin (ATRA).

In certain preferred embodiments, the compounds of the invention are administered in combination with a chemoprotective agent. Chemoprotective agents act to protect the body or minimize the side effects of chemotherapy. Examples of such agents include, but are not limited to, amfostine, mesna, and dexrazoxane.

In one aspect of the invention, the subject compounds are administered in combination with radiation therapy. Radiation is commonly delivered internally (implantation of radioactive material near cancer site) or externally from a machine that employs photon (x-ray or gamma-ray) or particle radiation. Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

It will be appreciated that compounds of the invention can be used in combination with an immunotherapeutic agent. One form of immunotherapy is the generation of an active systemic tumor-specific immune response of host origin by administering a vaccine composition at a site distant from the tumor. Various types of vaccines have been proposed, including isolated tumor-antigen vaccines and anti-idiotype vaccines. Another approach is to use tumor cells from the subject to be treated, or a derivative of such cells (reviewed by Schirrmacher et al. (1995) J. Cancer Res. Clin. Oncol. 121:487). In U.S. Pat. No. 5,484,596, Hanna Jr. et al. claim a method for treating a resectable carcinoma to prevent recurrence or metastases, comprising surgically removing the tumor, dispersing the cells with collagenase, irradiating the cells, and vaccinating the patient with at least three consecutive doses of about $10^7$ cells.

It will be appreciated that the compounds of the invention may advantageously be used in conjunction with one or more adjunctive therapeutic agents. Examples of suitable agents for adjunctive therapy include a $5HT_1$ agonist, such as a triptan (e.g. sumatriptan or naratriptan); an adenosine A1 agonist; an EP ligand; an NMDA modulator, such as a glycine antagonist; a sodium channel blocker (e.g. lamotrigine); a substance P antagonist (e.g. an $NK_1$ antagonist); a cannabinoid; acetaminophen or phenacetin; a 5-lipoxygenase inhibitor; a leukotriene receptor antagonist; a DMARD (e.g. methotrexate); gabapentin and related compounds; a tricyclic antidepressant (e.g. amitryptilline); a neurone stabilising antiepileptic drug; a mono-aminergic uptake inhibitor (e.g. venlafaxine); a matrix metalloproteinase inhibitor; a nitric oxide synthase (NOS) inhibitor, such as an iNOS or an nNOS inhibitor; an inhibitor of the release, or action, of tumour necrosis factor .alpha.; an antibody therapy, such as a monoclonal antibody therapy; an antiviral agent, such as a nucleoside inhibitor (e.g. lamivudine) or an immune system modulator (e.g. interferon); an opioid analgesic; a local anaesthetic; a stimulant, including caffeine; an $H_2$-antagonist (e.g. ranitidine); a proton pump inhibitor (e.g. omeprazole); an antacid (e.g. aluminium or magnesium hydroxide); an antiflatulent (e.g. simethicone); a decongestant (e.g. phenylephrine, phenylpropanolamine, pseudoephedrine, oxymetazoline, epinephrine, naphazoline, xylometazoline, propylhexedrine, or levo-desoxyephedrine); an antitussive (e.g. codeine, hydrocodone, carmiphen, carbetapentane, or dextramethorphan); a diuretic; or a sedating or non-sedating antihistamine.

Matrix metalloproteinases (MMPs) are a family of zinc-dependent neutral endopeptidases collectively capable of degrading essentially all matrix components. Over 20 MMP modulating agents are in pharmaceutical develop, almost half of which are indicated for cancer. The University of Toronto researchers have reported that HDACs regulate MMP expression and activity in 3T3 cells. In particular, inhibition of HDAC by trichostatin A (TSA), which has been shown to prevent tumorigenesis and metastasis, decreases mRNA as well as zymographic activity of gelatinase A (MMP2; Type IV collagenase), a matrix metalloproteinase, which is itself, implicated in tumorigenesis and metastasis (Ailenberg M., Silverman M., *Biochem Biophys Res Commun.* 2002, 298: 110-115). Another recent article that discusses the relationship of HDAC and MMPs can be found in Young D. A., et al., *Arthritis Research & Therapy*, 2005, 7: 503. Furthermore, the commonality between HDAC and MMPs inhibitors is their zinc-binding functionality. Therefore, in one aspect of the invention, compounds of the invention can be used as MMP inhibitors and may be of use in the treatment of disorders relating to or associated with dysregulation of MMP. The overexpression and activation of MMPs are known to induce tissue destruction and are also associated with a number of specific diseases including rheumatoid arthritis, periodontal disease, cancer and atherosclerosis.

The compounds may also be used in the treatment of a disorder involving, relating to or, associated with dysregulation of histone deacetylase (HDAC). There are a number of disorders that have been implicated by or known to be mediated at least in part by HDAC activity, where HDAC activity is known to play a role in triggering disease onset, or whose symptoms are known or have been shown to be alleviated by HDAC inhibitors. Disorders of this type that would be expected to be amenable to treatment with the compounds of the invention include the following but not limited to: Antiproliferative disorders (e.g. cancers); Neurodegenerative diseases including Huntington's Disease, Polyglutamine disease, Parkinson's Disease, Alzheimer's Disease, Seizures, Striatonigral degeneration, Progressive supranuclear palsy, Torsion dystonia, Spasmodic torticollis and dyskinesis, Familial tremor, Gilles de la Tourette syndrome, Diffuse Lewy body disease, Progressive supranuclear palsy, Pick's disease, intracerebral hemorrhage, Primary lateral sclerosis, Spinal muscular atrophy, Amyotrophic lateral sclerosis, Hypertrophic interstitial polyneuropathy, Retinitis pigmentosa, Hereditary optic atrophy, Hereditary spastic paraplegia, Progressive ataxia and Shy-Drager syndrome; Metabolic diseases including Type 2 diabetes; Degenerative Diseases of the Eye including Glaucoma, Age-related macular degeneration, Rubeotic glaucoma; Inflammatory diseases and/or Immune system disorders including Rheumatoid Arthritis (RA), Osteoarthritis, Juvenile chronic arthritis, Graft versus Host disease, Psoriasis, Asthma, Spondyloarthropathy, Crohn's Disease, inflammatory bowel disease Colitis Ulcerosa, Alcoholic hepatitis, Diabetes, Sjoegrens's syndrome, Multiple Sclerosis, Ankylosing spondylitis, Membranous glomerulopathy, Discogenic pain, Systemic Lupus Erythematosus; Disease involving angiogenesis including cancer, psoriasis, rheumatoid arthritis; Psychological disorders including bipolar disease, schizophrenia, mania, depression and dementia; Cardiovascular Diseases including heart failure, restenosis and arteriosclerosis; Fibrotic diseases including liver fibrosis, cystic fibrosis and angiofibroma; Infectious diseases including Fungal infections, such as Candida Albicans, Bacterial infections, Viral infections, such as Herpes Simplex, Protozoal infections, such as Malaria, *Leishmania* infection, Trypanosoma brucei infection, Toxoplasmosis and coccidlosis and Haematopoietic disorders including thalassemia, anemia and sickle cell anemia.

In one embodiment, compounds of the invention can be used to induce or inhibit apoptosis, a physiological cell death process critical for normal development and homeostasis. Alterations of apoptotic pathways contribute to the pathogenesis of a variety of human diseases. Compounds of the invention, as modulators of apoptosis, will be useful in the treatment of a variety of human diseases with abberations in apoptosis including cancer (particularly, but not limited to, follicular lymphomas, carcinomas with p53 mutations, hormone dependent tumors of the breast, prostate and ovary, and precancerous lesions such as familial adenomatous polyposis), viral infections (including, but not limited to, herpesvirus, poxvirus, Epstein-Barr virus, Sindbis virus and adenovirus), autoimmune diseases (including, but not limited to, systemic lupus, erythematosus, immune mediated glomerulonephritis, rheumatoid arthritis, psoriasis, inflammatory bowel diseases, and autoimmune diabetes mellitus), neurodegenerative disorders (including, but not limited to, Alzheimer's disease, AIDS-related dementia, Parkinson's disease, amyotrophic lateral sclerosis, retinitis pigmentosa, spinal muscular atrophy and cerebellar degeneration), AIDS, myelodysplastic syndromes, aplastic anemia, ischemic injury associated myocardial infarctions, stroke and reperfusion injury, arrhythmia, atherosclerosis, toxin-induced or alcohol induced liver diseases, hematological diseases (including, but not limited to, chronic anemia and aplastic anemia), degenerative diseases of the musculoskeletal system (including, but not limited to, osteoporosis and arthritis), aspirin-sensitive rhinosinusitis, cystic fibrosis, multiple sclerosis, kidney diseases, and cancer pain.

In one aspect, the invention provides the use of compounds of the invention for the treatment and/or prevention of immune response or immune-mediated responses and diseases, such as the prevention or treatment of rejection following transplantation of synthetic or organic grafting materials, cells, organs or tissue to replace all or part of the function of tissues, such as heart, kidney, liver, bone marrow, skin, cornea, vessels, lung, pancreas, intestine, limb, muscle, nerve tissue, duodenum, small-bowel, pancreatic-islet-cell, including xeno-transplants, etc.; to treat or prevent graft-versus-host disease, autoimmune diseases, such as rheumatoid arthritis, systemic lupus erythematosus, thyroiditis, Hashimoto's thyroiditis, multiple sclerosis, myasthenia gravis, type I diabetes uveitis, juvenile-onset or recent-onset diabetes mellitus, uveitis, Graves disease, psoriasis, atopic dermatitis, Crohn's disease, ulcerative colitis, vasculitis, auto-antibody mediated diseases, aplastic anemia, Evan's syndrome, autoimmune hemolytic anemia, and the like; and further to treat infectious diseases causing aberrant immune response and/or activation, such as traumatic or pathogen induced immune disregulation, including for example, that which are caused by hepatitis B and C infections, HIV, staphylococcus aureus infection, viral encephalitis, sepsis, parasitic diseases wherein damage is induced by an inflammatory response (e.g., leprosy); and to prevent or treat circulatory diseases, such as arteriosclerosis, atherosclerosis, vasculitis, polyarteritis nodosa and myocarditis. In addition, the present invention may be used to prevent/suppress an immune response associated with a gene therapy treatment, such as the introduction of foreign genes into autologous cells and expression of the encoded product. Thus in one embodiment, the invention relates to a method of treating an immune response disease or disorder or an immune-mediated response or disorder in a subject in need of treatment comprising administering to said subject a therapeutically effective amount of a compound of the invention.

In one aspect, the invention provides the use of compounds of the invention in the treatment of a variety of neurodegenerative diseases, a non-exhaustive list of which includes: I. Disorders characterized by progressive dementia in the absence of other prominent neurologic signs, such as Alzheimer's disease; Senile dementia of the Alzheimer type; and Pick's disease (lobar atrophy); II. Syndromes combining progressive dementia with other prominent neurologic abnormalities such as A) syndromes appearing mainly in adults (e.g., Huntington's disease, Multiple system atrophy combining dementia with ataxia and/or manifestations of Parkinson's disease, Progressive supranuclear palsy (Steel-Richardson-Olszewski), diffuse Lewy body disease, and corticodentatonigral degeneration); and B) syndromes appearing mainly in children or young adults (e.g., Hallervorden-Spatz disease and progressive familial myoclonic epilepsy); III. Syndromes of gradually developing abnormalities of posture and movement such as paralysis agitans (Parkinson's disease), striatonigral degeneration, progressive supranuclear palsy, torsion dystonia (torsion spasm; dystonia musculorum deformans), spasmodic torticollis and other dyskinesis, familial tremor, and Gilles de la Tourette syndrome; IV. Syndromes of progressive ataxia such as cerebellar degenerations (e.g., cerebellar cortical degeneration and olivopontocerebellar atrophy (OPCA)); and spinocerebellar degeneration (Friedreich's atazia and related disorders); V. Syndrome of central autonomic nervous system failure (Shy-Drager syndrome); VI. Syndromes of muscular weakness and wasting without sensory changes (motorneuron disease such as amyotrophic lateral sclerosis, spinal muscular atrophy (e.g., infantile spinal muscular atrophy (Werdnig-Hoffman), juvenile spinal muscular atrophy (Wohlfart-Kugelberg-Welander) and other forms of familial spinal muscular atrophy), primary lateral sclerosis, and hereditary spastic paraplegia; VII. Syndromes combining muscular weakness and wasting with sensory changes (progressive neural muscular atrophy; chronic familial polyneuropathies) such as peroneal muscular atrophy (Charcot-Marie-Tooth), hypertrophic interstitial polyneuropathy (Dejerine-Sottas), and miscellaneous forms of chronic progressive neuropathy; VIII. Syndromes of progressive visual loss such as pigmentary degeneration of the retina (retinitis pigmentosa), and hereditary optic atrophy (Leber's disease). Furthermore, compounds of the invention can be implicated in chromatin remodeling.

The invention encompasses pharmaceutical compositions comprising pharmaceutically acceptable salts of the compounds of the invention as described above. Examples of suitable salts include but are not limited to the hydrochloride, citrate or tartrate salt, preferably the tartrate salt. The invention also encompasses pharmaceutical compositions comprising solvates or hydrates of the compounds of the invention. The term "hydrate" includes but is not limited to hemihydrate, monohydrate, dihydrate, trihydrate and the like.

The invention further encompasses pharmaceutical compositions comprising any solid or liquid physical form of the compound of the invention. For example, the compounds can be in a crystalline form, in amorphous form, and have any particle size. The particles may be micronized, or may be agglomerated, particulate granules, powders, oils, oily suspensions or any other form of solid or liquid physical form.

The compounds of the invention, and derivatives, fragments, analogs, homologs, pharmaceutically acceptable salts or hydrate thereof can be incorporated into pharmaceutical compositions suitable for administration, together with a pharmaceutically acceptable carrier or excipient. Such compositions typically comprise a therapeutically effective amount of any of the compounds above, and a pharmaceutically acceptable carrier. Preferably, the effective amount when treating cancer is an amount effective to selectively induce terminal differentiation of suitable neoplastic cells and less than an amount which causes toxicity in a patient.

Compounds of the invention may be administered by any suitable means, including, without limitation, parenteral, intravenous, intramuscular, subcutaneous, implantation, oral, sublingual, buccal, nasal, pulmonary, transdermal, topical, vaginal, rectal, and transmucosal administrations or the like. Topical administration can also involve the use of transdermal administration such as transdermal patches or iontophoresis devices. Pharmaceutical preparations include a solid, semi-solid or liquid preparation (tablet, pellet, troche, capsule, suppository, cream, ointment, aerosol, powder, liquid, emulsion, suspension, syrup, injection etc.) containing a compound of the invention as an active ingredient, which is suitable for selected mode of administration. In one embodiment, the pharmaceutical compositions are administered orally, and are thus formulated in a form suitable for oral administration, i.e., as a solid or a liquid preparation. Suitable solid oral formulations include tablets, capsules, pills, granules, pellets, sachets and effervescent, powders, and the like. Suitable liquid oral formulations include solutions, suspensions, dispersions, emulsions, oils and the like. In one embodiment of the present invention, the composition is formulated in a capsule. In accordance with this embodiment, the compositions of the present invention comprise in addition to the active compound and the inert carrier or diluent, a hard gelatin capsule.

Any inert excipient that is commonly used as a carrier or diluent may be used in the formulations of the present invention, such as for example, a gum, a starch, a sugar, a cellulosic material, an acrylate, or mixtures thereof. A preferred diluent is microcrystalline cellulose. The compositions may further comprise a disintegrating agent (e.g., croscarmellose sodium) and a lubricant (e.g., magnesium stearate), and may additionally comprise one or more additives selected from a binder, a buffer, a protease inhibitor, a surfactant, a solubilizing agent, a plasticizer, an emulsifier, a stabilizing agent, a viscosity increasing agent, a sweetener, a film forming agent, or any combination thereof. Furthermore, the compositions of the present invention may be in the form of controlled release or immediate release formulations.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil. Solutions or suspensions can also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide.

In addition, the compositions may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate, Primogel), buffers (e.g., tris-HCI, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol, cyclodextrins), a glidant (e.g., colloidal silicon dioxide), anti-oxidants (e.g., ascorbic acid, sodium metabisulfite, butylated hydroxyanisole), stabilizers (e.g., hydroxypropyl cellulose, hydroxypropylmethyl cellulose), viscosity increasing agents (e.g., carbomer, colloidal silicon dioxide, ethyl cellulose, guar gum), sweeteners (e.g., sucrose, aspartame, citric acid), flavoring agents (e.g., peppermint, methyl salicylate, or orange flavoring), preservatives (e.g., Thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates) and/or adjuvants.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

In one preferred embodiment, the compound can be formulated in an aqueous solution for intravenous injection. In one embodiment, solubilizing agents can be suitably employed. A particularly preferred solubilizing agent includes cyclodextrins and modified cyclodextrins, such as sulfonic acid substituted β-cyclodextrin derivative or salt thereof. An example of such a solubilizing agent is sold under the trademark CAPTISOL® by CyDex, Inc. CAPTISOL is a polyanionic β-cyclodextrin derivative with a sodium sulfonate salt separated from the lipophilic cavity by a butyl ether spacer group, or sulfobutylether (SBE). The selection of the SBE7-β-CD as the cyclodextrin with the most desirable safety profile and drug carrier properties is based upon evaluations of the mono, tetra and hepta-substituted preparations (SBE1, SBE4, and SBE7). CAPTISOL is the trade name for CyDex's SBE7-β-CD PRODUCT.

Relative to β-cyclodextrin, the preferred solubilizing agents, such as CAPTISOL®, provide superior water solubility in excess of 70, preferably 90 grams/100 ml.

In one embodiment, the solubilizing agent is added to the aqueous solution in an amount of at least 15% weight/volume, preferably about 30% weight/volume. Additional optional excipients can include dextran in an amount of at least about 1% weight/volume, preferably about 5% weight/volume.

The pharmaceutical compositions can be included in a container, pack, or dispenser together with instructions for administration.

Daily administration may be repeated continuously for a period of several days to several years. Oral treatment may continue for between one week and the life of the patient. Preferably the administration may take place for five consecutive days after which time the patient can be evaluated to determine if further administration is required. The administration can be continuous or intermittent, e.g., treatment for a number of consecutive days followed by a rest period. The compounds of the present invention may be administered intravenously on the first day of treatment, with oral administration on the second day and all consecutive days thereafter.

The preparation of pharmaceutical compositions that contain an active component is well understood in the art, for example, by mixing, granulating, or tablet-forming processes. The active therapeutic ingredient is often mixed with excipients that are pharmaceutically acceptable and compatible with the active ingredient. For oral administration, the active agents are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions and the like as detailed above.

The amount of the compound administered to the patient is less than an amount that would cause toxicity in the patient. In certain embodiments, the amount of the compound that is administered to the patient is less than the amount that causes a concentration of the compound in the patient's plasma to equal or exceed the toxic level of the compound. Preferably, the concentration of the compound in the patient's plasma is maintained at about 10 nM. In one embodiment, the concentration of the compound in the patient's plasma is maintained at about 25 nM. In one embodiment, the concentration of the compound in the patient's plasma is maintained at about 50 nM. In one embodiment, the concentration of the compound in the patient's plasma is maintained at about 100 nM. In one embodiment, the concentration of the compound in the patient's plasma is maintained at about 500 nM. In one embodiment, the concentration of the compound in the patient's plasma is maintained at about 1000 nM. In one embodiment, the concentration of the compound in the patient's plasma is maintained at about 2500 nM. In one embodiment, the concentration of the compound in the patient's plasma is maintained at about 5000 nM. The optimal amount of the compound that should be administered to the patient in the practice of the present invention will depend on the particular compound used and the type of cancer being treated.

Definitions

Listed below are definitions of various terms used to describe this invention. These definitions apply to the terms as they are used throughout this specification and claims, unless otherwise limited in specific instances, either individually or as part of a larger group.

The term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about eight carbon atoms. Examples of such radicals include methyl, ethyl, n-propyl, isopropyl, n-butyl, isobutyl, sec-butyl, tert-butyl, pentyl, iso-amyl, hexyl and the like.

The term "alkenyl" embraces linear or branched radicals having at least one carbon-carbon double bond of two to about twenty carbon atoms or, preferably, two to about twelve carbon atoms. More preferred alkenyl radicals are "lower alkenyl" radicals having two to about ten and more preferably about two to about eight carbon atoms. Examples of alkenyl radicals include ethenyl, allyl, propenyl, butenyl and 4-methylbutenyl. The terms "alkenyl", and "lower alkenyl", embrace radicals having "cis" and "trans" orientations, or alternatively, "E" and "Z" orientations.

The term "alkynyl" embraces linear or branched radicals having at least one carbon-carbon triple bond of two to about twenty carbon atoms or, preferably, two to about twelve carbon atoms. More preferred alkynyl radicals are "lower alkynyl" radicals having two to about ten and more preferably two to about eight carbon atoms. Examples of alkynyl radicals include propargyl, 1-propynyl, 2-propynyl, 1-butyne, 2-butynyl and 1-pentynyl.

The term "alkoxy" embraces linear or branched oxy-containing radicals each having alkyl portions of one to about twenty carbon atoms or, preferably, one to about twelve carbon atoms. More preferred alkoxy radicals are "lower alkoxy" radicals having one to about ten and more preferably having one to about eight carbon atoms. Examples of such radicals include methoxy, ethoxy, propoxy, butoxy and tert-butoxy.

The term "alkoxyalkoxy" embraces alkoxy radicals having one or more alkoxy radicals attached to the alkyl radical, that is, to form monoalkoxyalkyl and dialkoxyalkyl radicals.

The term "compound" is defined herein to include pharmaceutically acceptable salts, solvates, hydrates, polymorphs, enantiomers, diastereoisomers, racemates and the like of the compounds having a formula as set forth herein.

The term "substituted" refers to the replacement of one or more hydrogen radicals in a given structure with the radical of a specified substituent including, but not limited to: halo, alkyl, alkenyl, alkynyl, aryl, heterocyclyl, thiol, alkylthio, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent can be further substituted.

The terms "halogen" or "halo" as used herein, refers to an atom selected from fluorine, chlorine, bromine and iodine.

As used herein, the term "aberrant proliferation" refers to abnormal cell growth.

The phrase "adjunctive therapy" encompasses treatment of a subject with agents that reduce or avoid side effects associated with the combination therapy of the present invention, including, but not limited to, those agents, for example, that reduce the toxic effect of anticancer drugs, e.g., bone resorption inhibitors, cardioprotective agents; prevent or reduce the incidence of nausea and vomiting associated with chemotherapy, radiotherapy or operation; or reduce the incidence of infection associated with the administration of myelosuppressive anticancer drugs.

The term "angiogenesis," as used herein, refers to the formation of blood vessels. Specifically, angiogenesis is a multi-step process in which endothelial cells focally degrade and invade through their own basement membrane, migrate through interstitial stroma toward an angiogenic stimulus, proliferate proximal to the migrating tip, organize into blood vessels, and reattach to newly synthesized basement membrane (see Folkman et al., Adv. Cancer Res., Vol. 43, pp. 175-203 (1985)). Anti-angiogenic agents interfere with this process. Examples of agents that interfere with several of these steps include thrombospondin-1, angiostatin, endostatin, interferon alpha and compounds such as matrix metalloproteinase (MMP) inhibitors that block the actions of enzymes that clear and create paths for newly forming blood vessels to follow; compounds, such as .alpha.v.beta 3 inhibitors, that interfere with molecules that blood vessel cells use to bridge between a parent blood vessel and a tumor; agents, such as specific COX-2 inhibitors, that prevent the growth of cells that form new blood vessels; and protein-based compounds that simultaneously interfere with several of these targets.

The term "apoptosis" as used herein refers to programmed cell death as signaled by the nuclei in normally functioning human and animal cells when age or state of cell health and condition dictates. An "apoptosis inducing agent" triggers the process of programmed cell death.

The term "cancer" as used herein denotes a class of diseases or disorders characterized by uncontrolled division of cells and the ability of these cells to invade other tissues, either by direct growth into adjacent tissue through invasion or by implantation into distant sites by metastasis.

The term "devices" refers to any appliance, usually mechanical or electrical, designed to perform a particular function.

As used herein, the term "dysplasia" refers to abnormal cell growth and typically refers to the earliest form of pre-cancerous lesion recognizable in a biopsy by a pathologist.

As used herein, the term "effective amount of the subject compounds," with respect to the subject method of treatment, refers to an amount of the subject compound which, when delivered as part of desired dose regimen, brings about, e.g. a change in the rate of cell proliferation and/or state of differentiation and/or rate of survival of a cell to clinically acceptable standards. This amount may further relieve to some extent one or more of the symptoms of a neoplasia disorder, including, but is not limited to: 1) reduction in the number of cancer cells; 2) reduction in tumor size; 3) inhibition (i.e., slowing to some extent, preferably stopping) of cancer cell infiltration into peripheral organs; 3) inhibition (i.e., slowing to some extent, preferably stopping) of tumor metastasis; 4) inhibition, to some extent, of tumor growth; 5) relieving or reducing to some extent one or more of the symptoms associated with the disorder; and/or 6) relieving or reducing the side effects associated with the administration of anticancer agents.

The term "hyperplasia," as used herein, refers to excessive cell division or growth.

The phrase an "immunotherapeutic agent" refers to agents used to transfer the immunity of an immune donor, e.g., another person or an animal, to a host by inoculation.

The term embraces the use of serum or gamma globulin containing performed antibodies produced by another individual or an animal; nonspecific systemic stimulation; adjuvants; active specific immunotherapy; and adoptive immunotherapy. Adoptive immunotherapy refers to the treatment of a disease by therapy or agents that include host inoculation of sensitized lymphocytes, transfer factor, immune RNA, or antibodies in serum or gamma globulin.

The term "inhibition," in the context of neoplasia, tumor growth or tumor cell growth, may be assessed by delayed appearance of primary or secondary tumors, slowed development of primary or secondary tumors, decreased occurrence of primary or secondary tumors, slowed or decreased severity of secondary effects of disease, arrested tumor growth and regression of tumors, among others. In the extreme, complete inhibition, is referred to herein as prevention or chemoprevention.

The term "metastasis," as used herein, refers to the migration of cancer cells from the original tumor site through the blood and lymph vessels to produce cancers in other tissues. Metastasis also is the term used for a secondary cancer growing at a distant site.

The term "neoplasm," as used herein, refers to an abnormal mass of tissue that results from excessive cell division. Neoplasms may be benign (not cancerous), or malignant (cancerous) and may also be called a tumor. The term "neoplasia" is the pathological process that results in tumor formation.

As used herein, the term "pre-cancerous" refers to a condition that is not malignant, but is likely to become malignant if left untreated.

The term "proliferation" refers to cells undergoing mitosis.

The phrase "EGFR-TK related disease or disorder" refers to a disease or disorder characterized by inappropriate EGFR-TK activity or over-activity of the EGFR-TK. Inappropriate activity refers to either: (i) EGFR-TK expression in cells which normally do not express EGFR-TKs; (ii) increased EGFR-TK expression leading to unwanted cell proliferation, differentiation and/or growth; or, (iii) decreased EGFR-TK expression leading to unwanted reductions in cell proliferation, differentiation and/or growth. Over-activity of EGFR-TKs refers to either amplification of the gene encoding a particular EGFR-TK or production of a level of EGFR-TK activity which can correlate with a cell proliferation, differentiation and/or growth disorder (that is, as the level of the EGFR-TK increases, the severity of one or more of the symptoms of the cellular disorder increases). Over activity can also be the result of ligand independent or constitutive activation as a result of mutations such as deletions of a fragment of an EGFR-TK responsible for ligand binding.

The phrase a "radio therapeutic agent" refers to the use of electromagnetic or particulate radiation in the treatment of neoplasia.

The term "recurrence" as used herein refers to the return of cancer after a period of remission. This may be due to incomplete removal of cells from the initial cancer and may occur locally (the same site of initial cancer), regionally (in vicinity of initial cancer, possibly in the lymph nodes or tissue), and/or distally as a result of metastasis.

The term "treatment" refers to any process, action, application, therapy, or the like, wherein a mammal, including a human being, is subject to medical aid with the object of improving the mammal's condition, directly or indirectly.

The term "vaccine" includes agents that induce the patient's immune system to mount an immune response against the tumor by attacking cells that express tumor associated antigens (Teas).

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical *Sciences,* 66: 1-19 (1977). The salts can be prepared in situ during the final isolation and purification of the compounds of the invention, or separately by reacting the free base function with a suitable organic acid or inorganic acid. Examples of pharmaceutically acceptable nontoxic acid addition salts include, but are not limited to, salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid lactobionic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to a compound of the invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al. (ed.) "Design and Application of Prodrugs, Textbook of Drug Design and Development, Chapter 5, 113-191 (1991); Bundgaard, et al., Journal of Drug Deliver Reviews, 8:1-38 (1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002). Examples of particularly preferred prodrugs include esters of the carboxylic acids of the invention. Preferred esters include aliphatic esters (e.g., alkyl, such as lower alkyl esters) and aromatic esters (such as phenyl esters). Other prodrugs include derivatives of the acid group that can be hydrolyzed in vivo.

As used herein, "pharmaceutically acceptable carrier" is intended to include any and all solvents, dispersion media, coatings, antibacterial and antifungal agents, isotonic and absorption delaying agents, and the like, compatible with pharmaceutical administration, such as sterile pyrogen-free water. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

As used herein, the term "pre-cancerous" refers to a condition that is not malignant, but is likely to become malignant if left untreated.

The term "subject" as used herein refers to an animal. Preferably the animal is a mammal. More preferably the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds described herein may contain one or more asymmetric centers and thus give rise to enantiomers, diastereomers, and other stereoisomeric forms that may be defined, in terms of absolute stereochemistry, as (R)— or (S)—, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers and/or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; cyclodextrins such as alpha- (α), beta- (β) and gamma- (γ) cyclodextrins; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as solubilizing agents, coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid; b) binders such as, for example, carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as, for example, cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al., and WO 98/43650 by Montgomery, all of which are incorporated herein by reference). A discussion of pulmonary delivery of antibiotics is also found in U.S. Pat. No. 6,014,969, incorporated herein by reference.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the formulae described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically excipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

Synthetic Methods

A quinazoline derivative of the formula I, or a pharmaceutically-acceptable salt thereof, may be prepared by any process known to be applicable to the preparation of chemically-related compounds. Suitable processes for making certain intermediates include, for example, those illustrated in European patent applications Nos. 0520722, 0566226, 0602851, 0635498, 0635507, U.S. Pat. Nos. 5,457,105, 5,770599, US Publication No. 2003/0158408 and reference such as, *J. Med. Chem.* 2004, 47, 871-887. Necessary starting materials may be obtained by standard procedures of organic chemistry. The preparation of such starting materials is described within the accompanying non-limiting Examples. Alternatively necessary starting materials are obtainable by analogous procedures to those illustrated which are within the ordinary skill of a chemist.

The compounds and processes of the present invention will be better understood in connection with the following representative synthetic schemes that illustrate the methods by which the compounds of the invention may be prepared, which are intended as an illustration only and not limiting of the scope of the invention. For simplicity, the scheme numbering preserves the numbering used in the priority applications.

Scheme 1

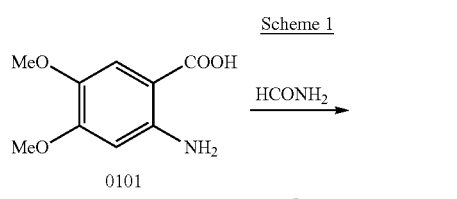

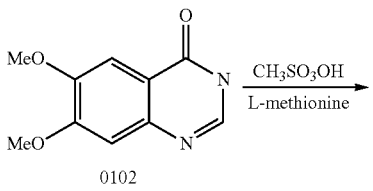

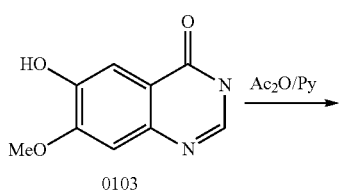

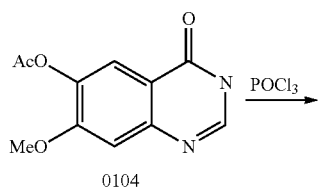

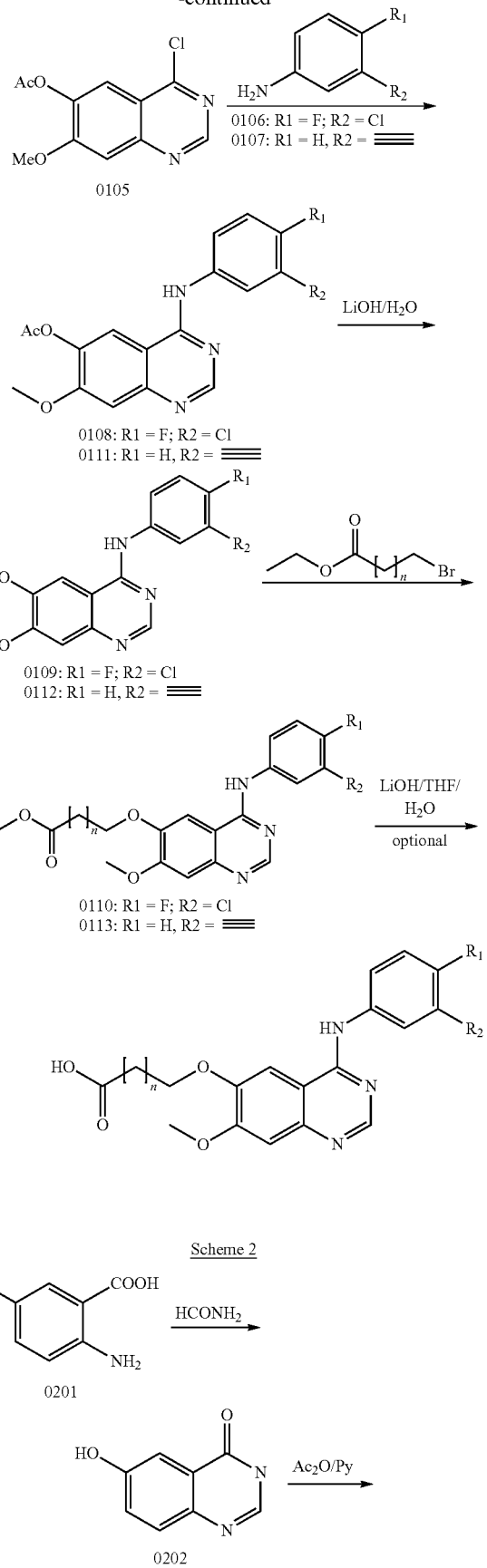

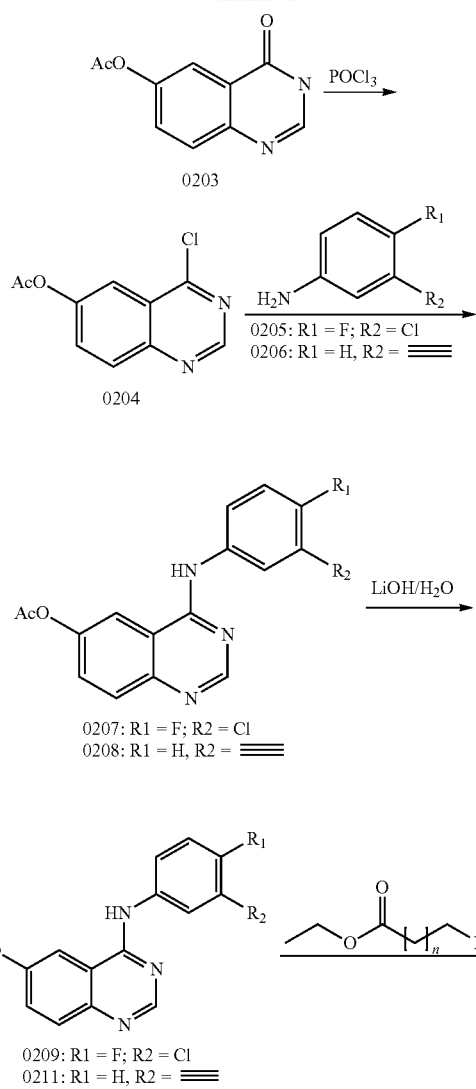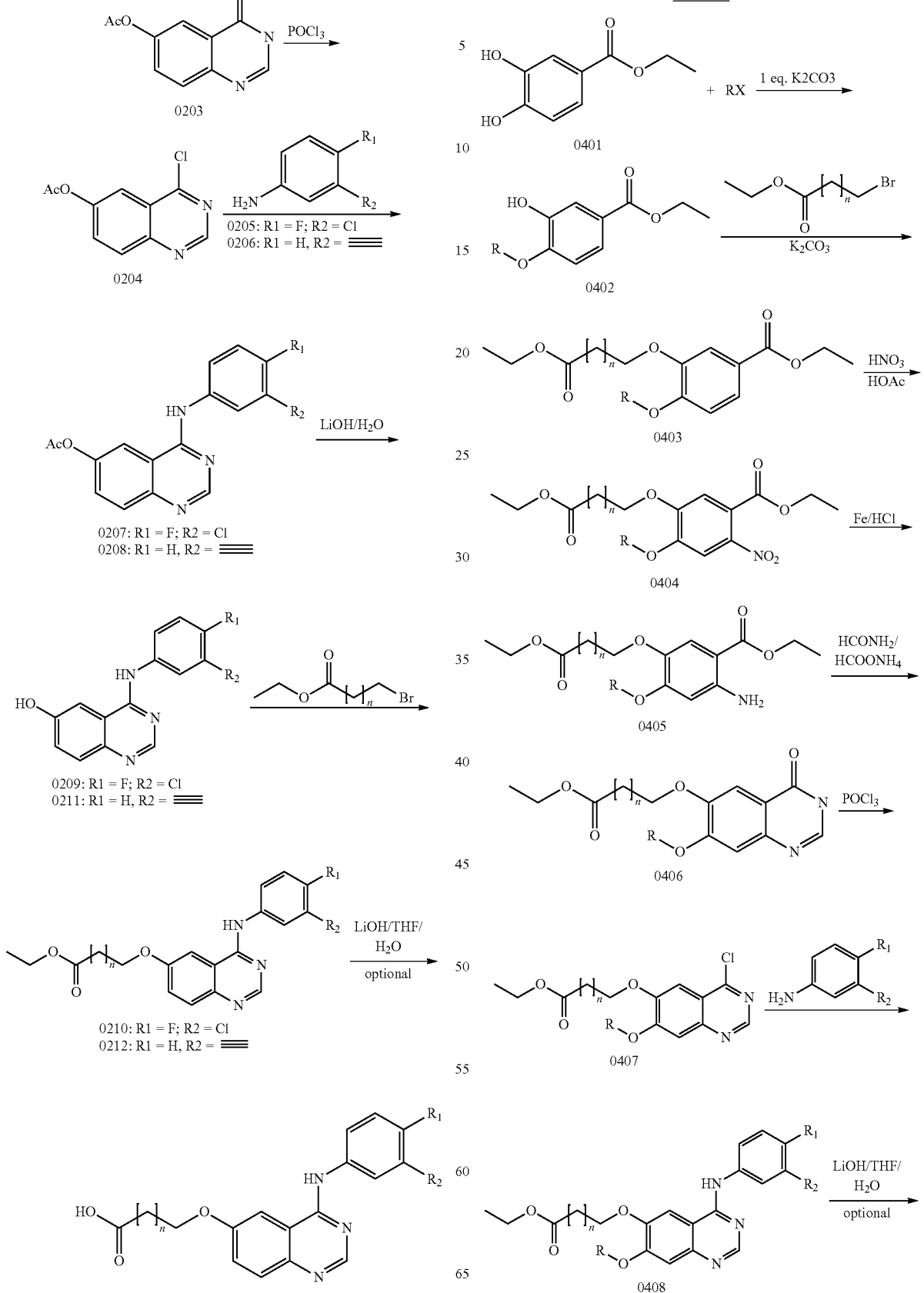

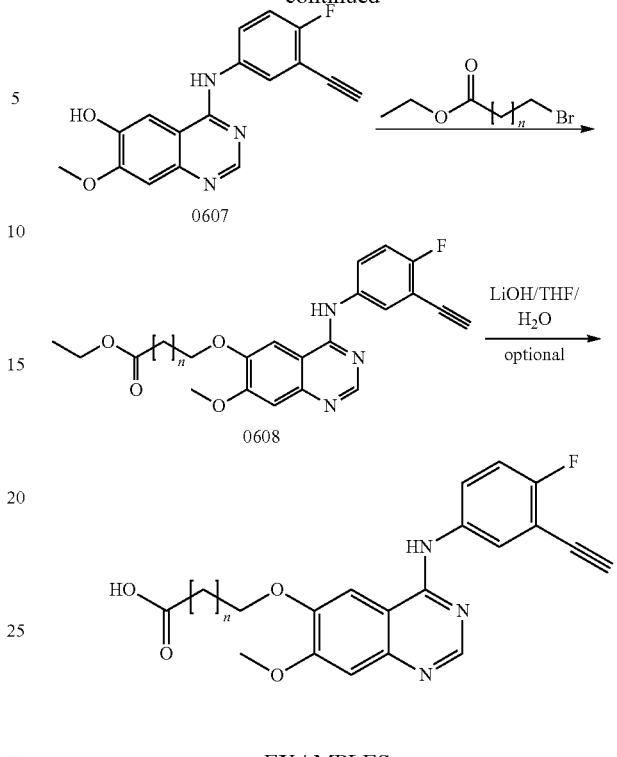

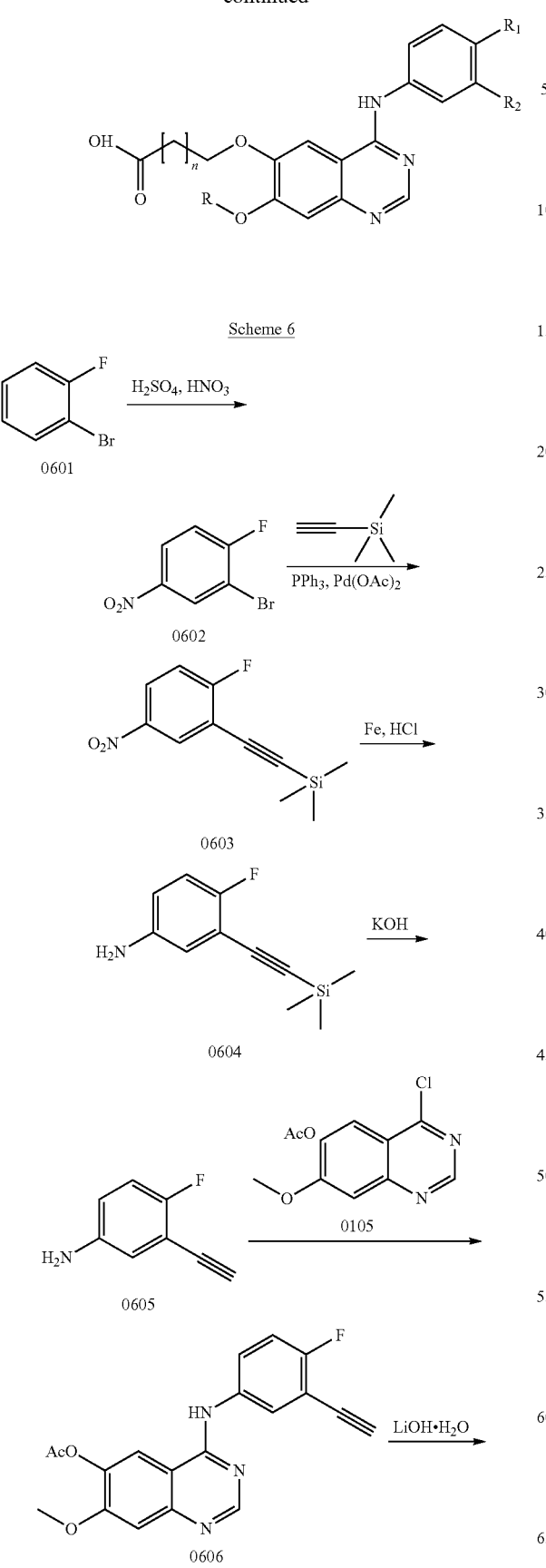

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

Preparation of 4-(3-Chloro-4-fluorophenylamino)-7-methoxyquinazolin-6-ol (Compound 0109)

Step 1a. 6,7-Dimethoxyquinazolin-4(3H)-one (Compound 0102)

A mixture of methyl 2-amino-4,5-dimethoxybenzoic acid 0101 (2.1 g, 10 mmol), ammonium formate (0.63 g, 10 mmol) and formamide (7 ml) was stirred and heated to 190~200° C. for 2 hours. Then the mixture was cooled to room temperature. The precipitate was isolated, washed with water and dried to provide the title compound 0102 as a brown solid (1.8 g, 84.7%): LCMS: m/z 207[M+1]$^+$; $^1$H NMR (DMSO) δ 3.87 (s, 3H), 3.89 (s, 3H), 7.12 (s, 1H), 7.43 (s, 1H), 7.97 (s, 1H), 12.08 (bs, 1H).

Step 1b. 6-Hydroxy-7-methoxyquinazolin-4(3H)-one (Compound 0103)

6,7-Dimethoxyquinazolin-4(3H)-one (0102) (10.3 g, 50 mmol) was added portionwise to stirred methanesulphonic acid (68 ml). L-Methionone (8.6 g, 57.5 mmol) was then added and resultant mixture was heated to 150~160° C. for 5 hours. The mixture was cooled to room temperature and poured onto a mixture (250 ml) of ice and water. The mixture was neutralized by the addition of aqueous sodium hydroxide solution (40%). The precipitate was isolated, washed with water and dried to yield title compound 0103 as a grey solid (10 g, crude): LCMS: m/z 193[M+1]$^+$.

Step 1c. 3,4-Dihydro-7-methoxy-4-oxoquinazolin-6-yl acetate (Compound 0104)

A mixture of 6-hydroxy-7-methoxyquinazolin-4(3H)-one (0103) (10 g crude), acetic anhydride (100 ml) and pyridine (8 ml) was stirred and heated to reflux for 3 hours. The mixture was cooled to room temperature and poured into a mixture (250 ml) of ice and water. The precipitate was isolated and dried to yield the title product 0104 as a grey solid (5.8 g, 50% two step overall yield): LCMS: m/z 235[M+1]$^+$; $^1$H NMR (CDCl$_3$) δ 2.27 (s, 3H), 3.89 (s, 3H), 7.28 (s, 1H), 7.72 (s, 1H), 8.08 (d, 1H), 12.20 (bs, 1H).

Step 1d. 4-Chloro-7-methoxyquinazolin-6-yl acetate (Compound 0105)

A mixture of 3,4-dihydro-7-methoxy-4-oxoquinazolin-6-yl acetate (0104) (2.0 g, 8.5 mmol) and phosphoryl trichloride (20 ml) was stirred and heated to reflux for 3 hours. When a clear solution was obtained, the excessive phosphoryl trichloride was removed under reduced pressure. The residue was dissolved in dichloromethane (50 ml) and the organic layer was washed with aqueous NaHCO$_3$ solution (20 ml×2) and brine (20 ml×1) and dried over MgSO$_4$, filtered and evaporated to give the title product 0105 as a yellow solid (1.4 g, 65%): LCMS: m/z 249[M+1]$^+$; $^1$H NMR (CDCl$_3$) δ 2.40 (s, 3H), 4.03 (s, 3H), 7.44 (s, 1H), 7.90 (s, 1H), 8.95 (bs, 1H).

Step 1e. 4-(3-Chloro-4-fluorophenylamino)-7-methoxyquinazolin-6-yl acetate hydrochloride (Compound 0108)

A mixture of 4-chloro-7-methoxyquinazolin-6-yl acetate (0105) (1.3 g, 5.1 mmol) and 3-chloro-4-fluorobenzenamine 0106 (1.5 g, 10.2 mmol) in isopropanol (45 ml) was stirred and heated to reflux for 3 hours. The mixture was cooled to room temperature and resulting precipitate was isolated. The solid was then dried to give the title compound 0108 as a light yellow solid (1.6 g, 79%): LCMS: m/z 362[M+1]$^+$; $^1$H NMR (DMSO) δ 2.36 (s, 3H), 3.98 (s, 3H), 7.49 (s, 1H), 7.52 (d, 1H), 7.72 (m, 1H), 8.02 (dd, 1H), 8.71 (s, 1H), 8.91 (s, 1H), 11.4 (bs, 1H).

Step 1f. 4-(3-Chloro-4-fluorophenylamino)-7-methoxyquinazolin-6-ol (Compound 0109)

A mixture of compound (0107) (1.41 g, 3.5 mmol), LiOH H$_2$O (0.5 g, 11.7 mmol) in methanol (100 ml) and H$_2$O (100 ml) was stirred at room temperature for 0.5 hour. The mixture was neutralized by addition of dilution acetic acid. The precipitate was isolated and dried to give the title compound 0109 as a grey solid (1.06 g, 94%): LCMS: m/z 320[M+1]$^+$; $^1$H NMR (DMSO) δ 3.99 (s, 3H), 7.20 (s, 1H), 7.38 (t, 1H), 7.75 (s, 1H), 7.81 (m, 1H), 8.20 (m, 1H), 8.46 (s, 1H), 9.46 (s, 1H), 9.68 (s, 1H).

Step 1g. Ethyl 2-(4-(3-chloro-4-fluorophenylamino)-7-methoxyquinazolin-6-yloxy)acetate (Compound 0110-1)

A mixture of compound 0109 (300 mg, 0.94 mmol) and Ethyl 2-bromoacetate (163 mg, 0.98 mmol) and potassium carbonate (323 mg, 2.35 mmol) in N,N-dimethylformamide (6 ml) was stirred and heated to 40° for 30 minutes. The reaction process was monitored by TLC. The mixture was filtrated. The filtration was concentrated under reduce pressure. The residues was wash with diethyl ether and dried to give the title compound 0110-1 as a yellow solid (280 mg, 74%): LCMS: m/z 406[M+1]$^+$; $^1$H NMR (DMSO) δ 1.23 (t, 3H), 3.96 (s, 3H), 4.20 (q, 2H), 4.95 (s, 2H), 7.24 (s, 1H), 7.44 (t, 1H), 7.75 (m, 1H), 7.82 (s, 1H), 8.10 (dd, 1H), 8.51 (s, 1H), 9.54 (s, 1H).

Example 2

Preparation of Ethyl 4-(4-(3-chloro-4-fluorophenylamino)-7-methoxyquinazolin-6-yloxy)butanoate (Compound 0110-3)

Step 2a. Ethyl 4-(4-(3-chloro-4-fluorophenylamino)-7-methoxyquinazolin-6-yloxy)butanoate (Compound 0110-3)

The title compound 0110-3 was prepared as a yellow solid (220 mg, 80.5%) from compound 0109 from step 1f (200 mg, 0.63 mmol) and ethyl 4-bromobutyrate (135 mg, 0.69 mmol) using a procedure similar to that described for compound 0110-1 (example 1): LCMS: m/z 434[M+1]$^+$; $^1$H NMR (CDCl$_3$) δ 1.36 (t, 3H), 2.23 (m, 2H), 2.57 (t, 2H), 4.03 (s, 3H), 4.32 (m, 4H), 7.15 (t, 1H), 7.25 (m, 1H), 7.87 (s, 1H), 8.00 (m, 2H), 8.15 (bs, 1H), 8.57 (s, 1H).

Example 3

Preparation of Ethyl 6-(4-(3-chloro-4-fluorophenylamino)-7-methoxyquinazolin-6-yloxy)hexanoate (Compound 0110-5)

Step 3a. Ethyl 6-(4-(3-chloro-4-fluorophenylamino)-7-methoxyquinazolin-6-yloxy)hexanoate (Compound 0110-5):

The title compound 0110-5 was prepared as a yellow solid (510 mg, 68%) from compound 0109 from step 1f (510 mg, 1.6 mmol) and ethyl 6-bromohexanoate (430 mg, 1.9 mmol) using a procedure similar to that described for compound 0110-1 (Example 1): LCMS: m/z 462[M+1]$^+$; $^1$H NMR (CDCl$_3$): δ 1.24 (t, 3H), 1.55 (m, 2H), 1.74 (m, 2H), 1.91 (m, 2H), 2.38 (m, 2H), 3.97 (s, 3H), 4.13 (m, 4H), 7.15 (t, 1H), 7.25 (m, 2H), 7.60 (m, 1H), 7.86 (m, 1H), 7.91 (dd, 1H), 8.61 (s, 1H).

Example 4

Preparation of Ethyl 7-(4-(3-chloro-4-fluorophenylamino)-7-methoxyquinazolin-6-yloxy)heptanoate (compound 0110-6)

Step 4a. Ethyl 7-(4-(3-chloro-4-fluorophenylamino)-7-methoxyquinazolin-6-yloxy)heptanoate (compound 0110-6)

The title compound 0110-6 was prepared as a yellow solid (390 mg, 53%) from compound 0109 from step 1f (512 mg, 1.6 mmol) and ethyl 7-bromoheptanoate (438 mg, 1.8 mmol) using a procedure similar to that described for compound 0110-1 (Example 1): LCMS: m/z 476[M+1]$^+$; $^1$H NMR (CDCl$_3$) δ 1.24 (t, 3H), 1.43 (m, 4H), 1.66 (m, 2H), 1.88 (m, 2H), 2.32 (t, 2H), 3.97 (s, 3H), 4.07 (t, 2H), 4.12 (q, 2H), 7.15 (t, 1H), 7.23 (t, 2H), 7.66 (m, 1H), 7.75 (m, 1H), 7.87 (dd, 1H), 8.65 (s, 1H).

Example 5

Preparation of 4-(3-Ethynylphenylamino)-7-methoxyquinazolin-6-ol (Compound 0112)

Step 5a.
4-(3-Ethynylphenylamino)-7-methoxyquinazolin-6-yl acetate Hydrochloride (Compound 0111)

A mixture of 4-chloro-7-methoxyquinazolin-6-yl acetate (0105) (2.6 g, 10.2 mmol) and 3-ethynylbenzenamine (0107) (2.4 g, 20.5 mmol) in isopropanol (100 ml) was stirred and heated to reflux for 3 hours. The mixture was cooled to room temperature. The precipitate was isolated and dried to give the title compound 0111 as a yellow solid (2.6 g, 68%): LCMS: m/z 334[M+1]$^+$; $^1$H NMR (DMSO) δ 2.39 (s, 3H), 3.17 (s, 1H), 3.98 (s, 3H), 7.35 (m, 1H), 7.40 (s, 1H), 7.47 (m, 1H), 7.72 (m, 1H), 7.90 (s, 1H), 8.57 (s, 1H), 8.87 (s, 1H), 10.99 (bs, 1H).

Step 5b.
4-(3-Ethynylphenylamino)-7-methoxyquinazolin-6-ol (Compound 0112)

A mixture of compound 0111 (2.0 g, 5.4 mmol) and LiOH H$_2$O (0.75 g, 17.9 mmol) in methanol (100 ml) and H$_2$O (100 ml) was stirred at room temperature for 0.5 hour. The mixture was neutralized by addition of dilution acetic acid. The precipitate was isolated and dried to give the title compound 0112 as a grey solid (1.52 g, 96%): LCMS: m/z 292[M+1]$^+$; $^1$H NMR (DMSO) δ 3.17 (s, 1H), 3.98 (s, 3H), 7.18 (d, 1H), 7.21 (s, 1H), 7.37 (t, 1H), 7.80 (s, 1H), 7.90 (d, 1H), 8.04 (m, 1H), 8.47 (s, 1H), 9.41 (s, 1H), 9.68 (bs, 1H).

Example 6

Preparation of Ethyl 4-(4-(3-ethynylphenylamino)-7-methoxyquinazolin-6-yloxy)butanoate (Compound 0113-9)

Step 6a. Ethyl 4-(4-(3-ethynylphenylamino)-7-methoxyquinazolin-6-yloxy)butanoate (Compound 0113-9)

The title compound 0113-9 was prepared as a yellow solid (438 mg, 59%) from compound 0112 (500 mg, 1.72 mmol) and ethyl 4-bromobutyrate (349 mg, 1.8 mmol) using a procedure similar to that described for compound 0110-1 (Example 1): LCMS: m/z 406[M+1]$^+$; $^1$H NMR (CDCl$_3$) δ 1.37 (t, 3H), 2.34 (m, 2H), 2.56 (t, 2H), 3.07 (s, 1H), 4.03 (s, 3H), 4.32 (m, 4H), 7.21 (m, 1H), 7.25 (s, 1H), 7.36 (t, 1H), 7.94 (s, 1H), 7.97 (m, 1H), 8.20 (s, 1H), 8.28 (m, 1H), 8.70 (s, 1H).

Example 7

Preparation of Ethyl 6-(4-(3-ethynylphenylamino)-7-methoxyquinazolin-6-yloxy)hexanoate (Compound 0113-11)

Step 7a. Ethyl 6-(4-(3-ethynylphenylamino)-7-methoxyquinazolin-6-yloxy)hexanoate (Compound 0113-11)

The title compound 0113-11 was prepared as yellow solid (543 mg, 73%) from compound 0112 from step 5b (500 mg, 1.72 mmol) and ethyl 6-bromohexanoate (401 mg, 1.8 mmol) using a procedure similar to that described for compound 0110-1 (Example 1): LCMS: m/z 434[M+1]$^+$; $^1$H NMR (CDCl$_3$) δ 1.24 (t, 3H), 1.53 (m, 2H), 1.72 (m, 2H), 1.90 (m, 2H), 2.37 (t, 3H), 3.08 (s, 1H), 3.97 (s, 3H), 4.10 (m, 4H), 7.19 (s, 1H), 7.25 (m, 2H), 7.34 (t, 1H), 7.67 (s, 1H), 7.78 (m, 1H), 7.84 (m, 1H), 8.67 (s, 1H).

Example 8

Preparation of Ethyl 6-(4-(3-ethynylphenylamino)-7-methoxyquinazolin-6-yloxy)heptanoate (Compound 0113-12)

Step 8a. Ethyl 6-(4-(3-ethynylphenylamino)-7-methoxyquinazolin-6-yloxy)heptanoate (Compound 0113-12)

The title compound 0113-12 was prepared as a yellow solid (305 mg, 84%) from compound 0112 from step 5b (247 mg, 0.85 mmol) and ethyl 7-bromohepanoate (211 mg, 0.89 mmol) using a procedure similar to that described for compound 0110-1 (Example 1): LCMS: 448 [M+1]$^+$; $^1$H NMR (CDCl$_3$): δ1.15 (t, J=7.5 Hz, 3H), 1.33-1.60 (m, 6H), 1.81 (m, 2H), 2.28 (t, J=7.5 Hz, 2H), 3.92 (s, 3H), 4.03 (q, J=7.2 Hz, 2H), 4.12 (t, J=6.6 Hz, 2H), 4.18 (s, 1H), 7.19 (m, 2H), 7.39 (t, J=7.8 Hz, 1H), 7.80 (s, 1H), 7.89 (d, J=8.1 Hz, 1H), 7.97 (s, 1H), 8.48 (s, 1H), 9.44 (s, 1H).

Example 8

Preparation of Ethyl 6-(4-(3-ethynylphenylamino)-7-methoxyquinazolin-6-yloxy)heptanoate (Compound 0408-12)

Step 8a'. Ethyl 3-hydroxy-4-methoxybenzoate (Compound 0402-12)

To a solution of ethyl 3,4-dihydroxybenzoate 0401 (12.52 g, 68.7 mmol) in DMF (50 mL) was added potassium carbonate (9.48 g, 68.7 mmol). After the mixture was stirred for 15 minutes, a solution of iodomethane (9.755 g, 68.7 mmol) in DMF (10 mL) was added dropwise. The reaction mixture was stirred at 20° C. for 24 hours. After reaction the mixture was filtered, and the filtrate was concentrated. The residue was dissolved in dichloromethane and washed with brine. The organic phase was dried over sodium sulfate, filtered and concentrated in vacuo to give crude product. The crude product was purified by column chromatography to give the title compound 0402-12 as a white solid (7.1 g, 53%): LCMS: 197 [M+1]$^+$, $^1$H NMR (DMSO-d$_6$): δ 1.29 (t, J=6.6 Hz, 3H), 3.83 (s, 3H), 4.25 (q, J=6.6 Hz, 2H), 7.00 (d, J=8.4 Hz, 1H), 7.38 (d, J=1.8 Hz, 1H), 7.43 (dd, J=8.4 Hz, 2.1 Hz, 1H), 9.36 (s, 1H).

Step 8b'. Ethyl 3-(7-ethoxy-7-oxoheptyloxy)-4-methoxybenzoate (Compound 0403-12)

A mixture of compound 0402-12 (6.34 g, 32.3 mmol), ethyl 7-bromoheptanoate (7.66 g, 32.3 mmol) and potassium carbonate (13.38 g, 96.9 mmol) in DMF (80 mL) was stirred at 60° C. for 3 hours. After reaction the mixture was filtrated. The filtrate was concentrated in vacuo and the residue was dissolved in dichloromethane and washed with brine twice. The organic phase was dried over sodium sulfate, filtered and concentrated to give the title product 0403-12 as a white solid (9.87 g, 86.7%): LCMS: 353 [M+1]$^+$, $^1$H NMR (DMSO-d$_6$): δ1.17 (t, J=6.9 Hz, 3H), 1.31 (t, J=7.2 Hz, 3H) 1.39 (m, 4H), 1.54 (m, 2H), 1.72 (m, 2H), 2.29 (t, J=7.2 Hz, 2H), 3.83 (s, 3H), 3.98 (t, J=7.2 Hz, 2H), 4.06 (q, J=6.9 Hz, 2H), 4.29 (q, J=7.2 Hz, 2H), 7.06 (d, J=8.4 Hz, 1H), 7.42 (d, J=1.8 Hz, 1H), 7.57 (dd, J=8.4 Hz, 1.8 Hz, 1H).

Step 8c'. Ethyl 5-(7-ethoxy-7-oxoheptyloxy)-4-methoxy-2-nitrobenzoate (Compound 0404-12)

Compound 0403-12 (9.87 g, 28.0 mmol) was dissolved in acetic acid (20 mL) and stirred at 20° C. Fuming nitric acid (17.66 g, 280.0 mmol) was added slowly dropwise. The mixture was stirred at 20° C. for 1 hour. After reaction the mixture was poured into ice-water and extracted with dichloromethane twice. The combined organic phase was washed with brine, aqueous NaHCO$_3$ solution and brine. The combined organic phase was dried over sodium sulfate, filtered and concentrated to give the title product 0404-12 as a yellow solid (10.75 g, 96.4%): LCMS: 398 [M+1]$^+$, $^1$H NMR (DMSO-d$_6$): δ 1.17 (t, J=7.2 Hz, 3H), 1.27 (t, J=7.2 Hz, 3H), 1.38 (m, 4H), 1.53 (m, 2H), 1.74 (m, 2H), 2.29 (t, J=7.2 Hz, 2H), 3.91 (s, 3H), 4.03 (q, J=7.2 Hz, 2H), 4.08 (t, J=6.3 Hz, 2H), 4.30 (q, J=7.2 Hz, 2H), 7.29 (s, 1H), 7.63 (s, 1H).

Step 8d'. Ethyl 2-amino-5-(7-ethoxy-7-oxoheptyloxy)-4-methoxybenzoate (Compound 0405-12)

A mixture of 0404-12 (10.75 g 27.0 mmol), ethanol (120 mL), water (40 mL) and hydrogen chloride (4 mL) was stirred to form a clear solution. The iron powder (15.16 g, 27.0 mmol) was added batchwise. The mixture was stirred at reflux for 30 min, and was then cooled to room temperature, adjusted pH to 8 with 10% sodium hydroxide solution, and filtered. The filtrate was concentrated to remove ethanol and extracted with dichloromethane twice. The combined organic phase was washed with brine and dried over sodium sulfate, filtered and concentrated to give the title product 0405-12 as a yellow solid (8.71 g, 87.8%): LCMS: 368 [M+1]$^+$, $^1$H NMR (DMSO-d$_6$): δ 1.17 (t, J=7.2 Hz, 3H), 1.28 (t, J=7.2 Hz, 3H), 1.37 (m, 4H), 1.53 (m, 2H), 1.66 (m, 2H), 2.29 (t, J=7.2 Hz, 2H), 3.74 (s, 3H), 3.78 (t, J=6.9 Hz, 2H), 4.06 (q, J=7.2 Hz, 2H), 4.22 (q, J=7.2 Hz, 2H), 6.35 (s, 1H), 6.44 (s, 2H), 7.15 (s, 1H).

Step 8e'. Ethyl 7-(7-methoxy-4-oxo-3,4-dihydroquinazolin-6-yloxy)heptanoate (Compound 0406-12)

A mixture of compound 0405-12 (8.71 g, 23.7 mmol), ammonium formate (1.48 g, 23.7 mmol) and formamide (40 mL) was stirred at 180° C. for 3 hours. After reaction the mixture was cooled to room temperature. The formamide was removed under reduce pressure, and the residue was dissolved in dichloromethane and washed with brine. The organic phase was dried over sodium sulfate, filtered and concentrated to give the title product 0406-12 as a pale white solid (8.18 g, 99%): LCMS: 349 [M+1]$^+$, $^1$H NMR (DMSO-d$_6$): δ1.17 (t, J=6.9 Hz, 3H), 1.38 (m, 4H), 1.55 (m, 2H), 1.75 (m, 2H), 2.29 (t, J=7.2 Hz, 2H), 3.90 (s, 3H), 4.05 (m, 4H), 7.13 (s, 1H), 7.42 (s, 1H), 7.97 (d, J=3.6 Hz, 1H), 12.07 (s, 1H).

Step 8f'. Ethyl 7-(4-chloro-7-methoxyquinazolin-6-yloxy)heptanoate (Compound 0407-12)

A mixture of product 0406-12 (8.18 g, 23.5 mmol) and phosphoryl trichloride (50 mL) was stirred at reflux for 4 hours. After reaction the excessive phosphoryl trichloride was removed under reduced pressure. The residue was dissolved in dichloromethane and washed with water, aqueous NaHCO$_3$ solution and brine. The organic phase was dried over sodium sulfate, filtered and concentrated to give the title product 0407-12 as a yellow solid (5.93 g, 69.7%): LCMS: 367 [M+1]$^+$, $^1$H NMR (DMSO-d$_6$): δ1.17 (t, J=6.9 Hz, 3H), 1.38 (m, 4H), 1.54 (m, 2H), 1.81 (m, 2H), 2.30 (t, J=7.2 Hz, 2H), 4.02 (s, 3H), 4.06 (q, J=6.9 Hz, 2H), 4.18 (t, J=6.3 Hz, 2H), 7.37 (s, 1H), 7.45 (s, 1H), 8.87 (s, 1H).

Step 8g'. Ethyl 7-(4-(3-ethynylphenylamino)-7-methoxyquinazolin-6-yloxy)heptanoate (Compound 0408-12)

A mixture of product 0407-12 (5.93 g, 16.4 mmol) and 3-ethynylbenzenamine (1.92 g, 16.4 mmol) in isopropanol (80 mL) was stirred at reflux 4 hours. After reaction the mixture was cooled to room temperature and resulting precipitate was isolated, washed with isopropanol and ether, and dried to give the title compound 0408-12 as a yellow solid (4.93 g, 67.1%): LCMS: 448 [M+1]$^+$, $^1$H NMR (DMSO-d$_6$): δ1.16 (t, J=7.2 Hz, 3H), 1.36-1.59 (m, 6H), 1.80 (m, 2H), 2.29 (t, J=7.2 Hz, 2H), 3.93 (s, 3H), 4.04 (q, J=6.9 Hz, 2H), 4.13 (t, J=6.6 Hz, 2H), 4.19 (s, 1H), 7.20 (m, 2H), 7.39 (t, J=7.8 Hz, 1H), 7.81 (s, 1H), 7.89 (d, J=8.4 Hz, 1H), 7.97 (s, 1H), 8.48 (s, 1H), 9.45 (s, 1H).

Example 9

Preparation of Ethyl 2-(4-(3-chloro-4-fluorophenylamino)quinazolin-6-yloxy)acetate (Compound 0210-13)

Step 9a. 6-Hydroxyquinazolin-4(3H)-one (compound 0202)

To a solution of 2-amino-5-hydroxybenzoic acid 0201 (30.6 g, 0.2 mol) in formamide was stirred and heated to 190° C. for 0.5 h. The mixture was allowed to cool to room temperature. The precipitate was isolated, washed with ether and dried to obtain title compound 0202 (32 g, brown solid, yield: 99%): LC-MS m/z 163 [M+1];
$^1$H NMR (DMSO) δ7.25 (dd, 1H), 7.40 (d, 1H), 7.46 (d, 1H), 7.88 (s, 1H).

Step 9b. 3,4-Dihydro-4-oxoquinazolin-6-yl acetate (Compound 0203)

A mixture of compound 0202 (30.0 g, 0.185 mol) and pyridine (35 ml) in acetic anhydride (275 ml) was stirred and heated at 100° C. for 2 hours. The reaction was poured into a mixture of ice and water (500 ml). The precipitate was isolated, washed with water and dried to obtain the title compound 0203 (24 g, pale white solid, yield: 61%): LC-MS m/z 205 [M+1]+; 1H-NMR (DMSO) δ 2.32 (s, 3H), 7.50 (dd, 1H), 7.80 (d, 1H), 7.98 (s, 1H), 8.02 (s, 1H).

Step 9c. 4-Chloroquinazolin-6-yl acetate (Compound 0204)

A mixture of compound 0203 (20.0 g, 0.1 mol) in POCl$_3$ (150 ml) was stirred and heated to reflux for 2 hours. The reaction was evaporated and the residue was partitioned between ethyl acetate and a saturated aqueous NaHCO$_3$ solution. The organic phase was washed with water, dried over Na$_2$SO$_4$ and evaporated. The mixture was purified by column chromatography (silica gel, elution: 1:2=ethyl acetate/petroleum) to obtained the title compound 0204 (7.5 g, white solid, yield: 35%): LC-MS m/z 223 [M+1]; $^1$H-NMR (CDCl$_3$) δ2.40 (s, 3H), 7.74 (dd, 1H), 8.00 (d, 1H), 8.09 (d, 1H), 9.05 (s, 1H).

Step 9d.
4-(3-Chloro-4-fluorophenylamino)quinazolin-6-yl acetate (Compound 0207)

A mixture of 0204 (1.0 g, 4.5 mmol) and 3-chloro-4-fluorobenzenamine 0205 (0.7 g, 5.0 mmol) in isopropanol (45 ml) was stirred and heated at 90° C. for 1 hours. The reaction was cooled to room temperature and the precipitate was isolated. The solid was washed in turn with isopropanol and methanol, dried to provide the title compound 0207 (1.3 g, pale yellow solid, yield: 87%): LC-MS m/z 332 [M+1]; 1H-NMR (DMSO) δ2.37 (s, 3H), 7.54 (t, 1H), 7.75 (m, 1H), 7.94 (dd, 1H), 7.99 (s, 1H), 8.02 (m, 1H), 8.64 (s, 1H), 8.95 (s, 1H).

Step 9e.
4-(3-Chloro-4-fluorophenylamino)quinazolin-6-ol (Compound 0209)

A mixture of 0207 (0.8 g, 2.6 mmol) and lithium hydroxide monohydrate (0.13 g, 3.2 mmol) in methanol (10 ml)/water (15 ml) was stirred at room temperature for 1 hour. The pH was adjusted to 4 with acetic acid and filtered. The collected yellow solid was washed by water and dried to obtained title compound 0209 (0.6 g, yellow solid, yield: 88%): LC-MS m/z 290 [M+1]; $^1$H-NMR (DMSO) δ7.42 (s, 1H), 7.45 (m, 1H), 7.70 (d, 1H), 7.76 (s, 1H), 7.86 (m, 1H), 8.24 (q, 1H), 8.48 (s, 1H), 9.61 (s, 1H).

Step 9f. Ethyl 2-(4-(3-chloro-4-fluorophenylamino) quinazolin-6-yloxy)acetate (Compound 0210-13)

A mixture of 0209 (0.2 g, 0.77 mmol), ethyl 3-bromopropanoate (0.14 g, 0.85 mmol) and K$_2$CO$_3$ (0.8 g, 5.8 mmol) in DMF (15 ml) was stirred and heated to 80° C. for 2 hours. The reaction was filtered and the filtrate was evaporated. The resulting solid was washed with ether to obtain the title compound 0210-13 (0.2 g, yellow solid, yield: 75%): mp 161-163° C.; LC-MS m/z 376 [M+1]; 1H-NMR (DMSO) δ1.20 (t, 3H), 4.20 (q, 2H), 4.96 (s, 2H), 7.45 (t, 1H), 7.55 (dd, 1H), 7.78 (m, 2H), 7.94 (d, 1H), 8.16 (dd, 1H), 8.54 (s, 1H), 9.69 (s, 1H).

Example 10

Preparation of Ethyl 4-(4-(3-chloro-4-fluorophenylamino)quinazolin-6-yloxy)-N-Hydroxybutanoate The title compound was prepared (20 mg) from compound 0209 from step 9e and ethyl 4-bromobutanoate using a procedure similar to that described for Example 9: mp 128-132° C.; LC-MS m/z 391 [M+1]; $^1$H-NMR (DMSO+D2O) δ2.05 (m, 2H), 2.24 (t, 2H), 4.21 (t, 2H) 7.46 (t, 1H), 7.54 (dd, 1H), 7.65 (m, 1H), 7.76 (d, 1H), 7.82 (m, 1H), 7.99 (m, 1H), 8.43 (s, 1H).

Example 11

Preparation of Ethyl 6-(4-(3-chloro-4-fluorophenylamino)quinazolin-6-yloxy)hexanoate (compound 0210-17)

Step 11a. Ethyl 6-(4-(3-chloro-4-fluorophenylamino) quinazolin-6-yloxy)hexanoate (compound 0210-17)

The title compound 0210-17 (0.2 g) was prepared from compound 0209 4-(3-chloro-4-fluorophenylamino)quinazolin-6-ol and ethyl 6-bromohexanoate using a procedure similar to that described for compound 0210-13 (Example 9): LC-MS m/z 433 [M+1], $^1$H-NMR (DMSO) δ1.13 (t, 3H), 1.45 (m, 2H), 1.60 (m, 2H), 1.76 (m, 2H), 2.30 (t, 2H), 4.05 (q, 2H), 4.11 (t, 2H), 7.41 (d, 1H), 7.45 (dd, 1H), 7.68 (d, 1H), 7.80 (m, 1H), 7.86 (m, 1H), 8.13 (dd, 1H), 8.48 (s, 1H).

Example 12

Preparation of Ethyl 7-(4-(3-chloro-4-fluorophenylamino)quinazolin-6-yloxy)heptanoate (Compound 0210-18)

Step 12a. Ethyl 7-(4-(3-chloro-4-fluorophenylamino) quinazolin-6-yloxy)heptanoate (Compound 0210-18)

The title compound 0210-18 (0.2 g) was prepared from compound 2-6 4-(3-chloro-4-fluorophenylamino)quinazolin-6-ol (0209) of step 9e and ethyl 7-bromoheptanoate using a procedure similar to that described for compound 0210-13 (Example 9): LC-MS m/z 420 [M+1], $^1$H-NMR (DMSO) δ1.13 (t, 3H), 1.36 (m, 2H), 1.46 (m, 2H), 1.54 (m, 2H), 1.78 (m, 2H), 2.27 (t, 2H), 4.05 (q, 2H), 4.11 (t, 2H), 7.41 (d, 1H), 7.47 (dd, 1H), 7.70 (d, 1H), 7.81 (m, 1H), 7.84 (m, 1H), 8.13 (dd, 1H), 8.50 (s, 1H).

Biological Assays:

As stated hereinbefore the derivatives defined in the present invention possess anti-proliferation activity. These properties may be assessed, for example, using one or more of the procedures set out below:

(a) An In Vitro Assay which Determines the Ability of a Test Compound to Inhibit EGFR Kinase.

The ability of compounds to inhibit receptor kinase (EGFR) activity can be assayed using HTSCAN™ EGF Receptor Kinase Assay Kits (Cell Signaling Technologies, Danvers, Mass.). EGFR tyrosine kinase is obtained as GST-kinase fusion protein which is produced using a baculovirus expression system with a construct expressing human EGFR (His672-Ala1210) (GenBank Accession No. NM_005228) with an amino-terminal GST tag. The protein is purified by one-step affinity chromatography using glutathione-agarose. An anti-phosphotyrosine monoclonal antibody, P-Tyr-100, is used to detect phosphorylation of biotinylated substrate peptides (EGFR, Biotin-PTP1B (Tyr66)). Enzymatic activity is tested in 60 mM HEPES, 5 mM MgCl$_2$ 5 mM MnCl$_2$ 200 M μATP, 1.25 mM DTT, 3 μM Na$_3$VO$_4$, 1.5 mM peptide, and 50 ng EGF Receptor Kinase. Bound antibody is detected using the DELFIA system (PerkinElmer, Wellesley, Mass.) consisting of DELFIA® Europium-labeled Anti-mouse IgG (PerkinElmer, #AD0124), DELFIA® Enhancement Solution (PerkinElmer, #1244-105), and a DELFIA® Streptavidin coated, 96-well Plate (PerkinElmer, AAAND-0005). Fluorescence is measured on a WALLAC Victor 2 plate reader and reported as relative fluorescence units (RFU). Data can be plotted using GraphPad Prism (v4.0a) and IC50's calculated using a sigmoidal dose response curve fitting algorithm.

Test compounds are dissolved in dimethylsulphoxide (DMSO) to give a 20 mM working stock concentration. Each assay is setup as follows: Added 100 μl of 10 mM ATP to 1.25 ml 6 mM substrate peptide. Dilute the mixture with $dH_2O$ to 2.5 ml to make 2×ATP/substrate cocktail ([ATP]=400 mM, [substrate]=3 mM). Immediately transfer enzyme from −80° C. to ice. Allow enzyme to thaw on ice. Microcentrifuge briefly at 4° C. to bring liquid to the bottom of the vial. Return immediately to ice. Add 10 μl of DTT (1.25 mM) to 2.5 ml of 4× HTScan™ Tyrosine Kinase Buffer (240 mM HEPES pH 7.5, 20 mM $MgCl_2$, 20 mM MnCl, 12 mM $NaVO_3$) to make DTT/Kinase buffer. Transfer 1.25 ml of DTT/Kinase buffer to enzyme tube to make 4× reaction cocktail ([enzyme]=4 ng/4 in 4× reaction cocktail). Incubate 12.5 μl of the 4× reaction cocktail with 12.5 μl/well of prediluted compound of interest (usually around 10 μM) for 5 minutes at room temperature. Add 25 μl of 2×ATP/substrate cocktail to 25 μl/well preincubated reaction cocktail/compound. Incubate reaction plate at room temperature for 30 minutes. Add 50 μl/well Stop Buffer (50 mM EDTA, pH 8) to stop the reaction. Transfer 25 μl of each reaction and 75 μl $dH_2O$/well to a 96-well streptavidin-coated plate and incubated at room temperature for 60 minutes. Wash three times with 200 μl/well PBS/T (PBS, 0.05% Tween-20). Dilute primary antibody, Phospho-Tyrosine mAb (P-Tyr-100), 1:1000 in PBS/T with 1% bovine serum albumin (BSA). Add 100 μl/well primary antibody. Incubate at room temperature for 60 minutes. Wash three times with 200 μl/well PBS/T. Dilute Europium labeled anti-mouse IgG 1:500 in PBS/T with 1% BSA. Add 100 μl/well diluted antibody. Incubate at room temperature for 30 minutes. Wash five times with 200 μl/well PBS/T. Add 100 μl/well DELFIA® Enhancement Solution. Incubate at room temperature for 5 minutes. Detect 615 nm fluorescence emission with appropriate Time-Resolved Plate Reader.

(b) An In Vitro Assay which Determines the Ability of a Test Compound to Inhibit the EGF-Stimulated EGFR Phosphorylation.

Allow A431 cell growth in a T75 flask using standard tissue culture procedures until cells reach near confluency (~1.5× $10^7$ cells; D-MEM, 10% FBS). Under sterile conditions dispensed 100 μl of the cell suspension per well in 96-well microplates (x cells plated per well). Incubate cells and monitor cell density until confluency is achieved with well-to-well consistency; approximately three days. Remove complete media from plate wells by aspiration or manual displacement. Replace media with 50 μl of pre-warmed serum free media per well and incubated 4 to 16 hours. Make two fold serial dilutions of inhibitor using pre-warmed D-MEM so that the final concentration of inhibitor range from 10 μM to 90 μM. Remove media from A431 cell plate. Add 100 μl of serial diluted inhibitor into cells and incubate 1 to 2 hours. Remove inhibitor from plate wells by aspiration or manual displacement. Add either serum free media for resting cells (mock) or serum free media with 100 ng/ml EGF. Use 100 μl of resting/activation media per well. Allow incubation at 37° C. for 7.5 minutes. Remove activation or stimulation media manually or by aspiration. Immediately fix cells with 4% formaldehyde in 1×PBS. Allow incubation on bench top for 20 minutes at RT with no shaking Wash five times with 1×PBS containing 0.1% Triton X-100 for 5 minutes per Wash. Remove Fixing Solution. Using a multi-channel pipettor, add 200 μl of Triton Washing Solution (1×PBS+0.1% Triton X-100). Allow wash to shake on a rotator for 5 minutes at room temperature. Repeat washing steps 4 more times after removing wash manually. Using a multi-channel pipettor, block cells/wells by adding 100 μl of LI-COR Odyssey Blocking Buffer to each well. Allow blocking for 90 minutes at RT with moderate shaking on a rotator. Add the two primary antibodies into a tube containing Odyssey Blocking Buffer. Mix the primary antibody solution well before addition to wells (Phospho-EGFR Tyr1045, Rabbit; 1:100 dilution; Cell Signaling Technology, 2237; Total EGFR, Mouse; 1:500 dilution; Biosource International, AHR5062). Remove blocking buffer from the blocking step and added 40 μl of the desired primary antibody or antibodies in Odyssey Blocking Buffer to cover the bottom of each well. Add 100 μl of Odyssey Blocking Buffer only to control wells. Incubate with primary antibody overnight with gentle shaking at RT. Wash the plate five times with 1×PBS+ 0.1% Tween-20 for 5 minutes at RT with gentle shaking, using a generous amount of buffer. Using a multi-channel pipettor add 200 μl of Tween Washing Solution. Allow wash to shake on a rotator for 5 minutes at RT. Repeat washing steps 4 more times. Dilute the fluorescently labeled secondary antibody in Odyssey Blocking Buffer (Goat anti-mouse IRDye™ 680 (1:200 dilution; LI-COR Cat.# 926-32220) Goat anti-rabbit IRDye™ 800CW (1:800 dilution; LI-COR Cat.# 926-32211). Mix the antibody solutions well and added 40 μl of the secondary antibody solution to each well. Incubate for 60 minutes with gentle shaking at RT. Protect plate from light during incubation. Wash the plate five times with 1×PBS+ 0.1% Tween-20 for 5 minutes at RT with gentle shaking, using a generous amount of buffer. Using a multi-channel pipettor add 200 μl of Tween Washing Solution. Allow wash to shake on a rotator for 5 minutes at RT. Repeat washing steps 4 more times. After final wash, remove wash solution completely from wells. Turned the plate upside down and tap or blot gently on paper towels to remove traces of wash buffer. Scan the plate with detection in both the 700 and 800 channels using the Odyssey Infrared Imaging System (700 nm detection for IRDye™ 680 antibody and 800 nm detection for IRDye™ 800CW antibody). Determine the ratio of total to phosphorylated protein (700/800) using Odyssey software and plot the results in Graphpad Prism (V4.0a). Data can be plotted using GraphPad Prism (v4.0a) and IC50's calculated using a sigmoidal dose response curve fitting algorithm.

(c) An In Vitro Assay which Determines the Ability of a Test Compound to Inhibit HDAC Enzymatic Activity.

HDAC inhibitors are screened using an HDAC fluorimetric assay kit (AK-500, Biomol, Plymouth Meeting, Pa.). Test compounds can be dissolved in dimethylsulphoxide (DMSO) to give a 20 mM working stock concentration. Fluorescence is measured on a WALLAC Victor 2 plate reader and reported as relative fluorescence units (RFU). Data are plotted using GraphPad Prism (v4.0a) and IC50's calculated using a sigmoidal dose response curve fitting algorithm.

Each assay is setup as follows: Defrost all kit components and keep on ice until use. Dilute HeLa nuclear extract 1:29 in Assay Buffer (50 mM Tris/Cl, pH 8.0, 137 mM NaCl, 2.7 mM KCl, 1 mM MgCl2). Prepare dilutions of Trichostatin A (TSA, positive control) and test compounds in assay buffer (5× of final concentration). Dilute Fluor de Lys™ Substrate in assay buffer to 100 uM (50 fold=2× final). Dilute Fluor de Lys™ developer concentrate 20-fold (e.g. 50 μl plus 950 μl Assay Buffer) in cold assay buffer. Second, dilute the 0.2 mM Trichostatin A 100-fold in the 1× Developer (e.g. 10 μl in 1 ml; final Trichostatin A concentration in the 1× Developer=2 μM; final concentration after addition to HDAC/Substrate reaction=1 μM). Add Assay buffer, diluted trichostatin A or test inhibitor to appropriate wells of the microtiter plate. Add diluted HeLa extract or other HDAC sample to all wells except for negative controls. Allow diluted Fluor de Lys™ Substrate and the samples in the microtiter plate to equilibrate to assay temperature (e.g. 25 or 37° C. Initiate HDAC reactions by adding diluted substrate (25 μl) to each well and mixing thoroughly. Allow HDAC reactions to proceed for 1 hour and then stopped them by addition of Fluor de Lys™ Developer (50 μl). Incubate plate at room temperature (25° C.) for 10-15 min. Read samples in a microtiter-plate reading fluorimeter capable of excitation at a wavelength in the range 350-380 nm and detection of emitted light in the range 440-460 nm.

The following compounds in TABLE B were screened in assays substantially as described above. The results are presented below. In these assays, the following grading was used: I≧10 μM, 10 μM>II>1 μM, 1 μM>III>0.1 μM, and IV≦0.1 μM for $IC_{50}$.

TABLE B

| Structure | IC50 (nM) | | |
|---|---|---|---|
| | HDAC | EGFR | HER2/ErbB2 |
| 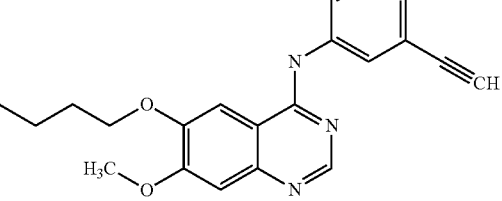 | | IV | |
| 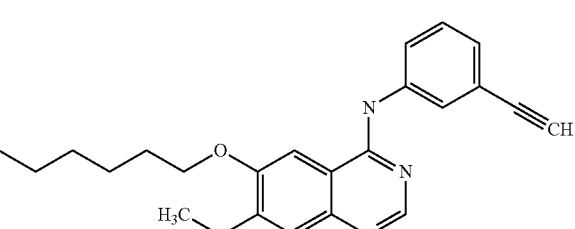 | I | IV | III |
| 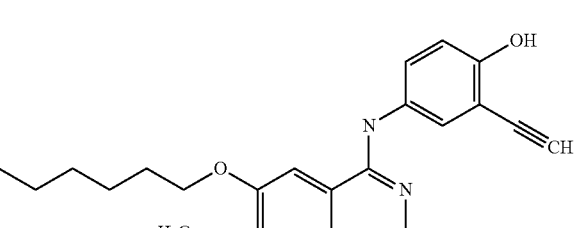 | I | IV | |
| 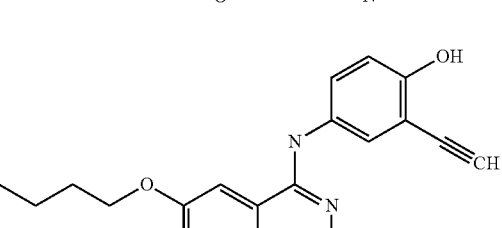 | I | | |
| 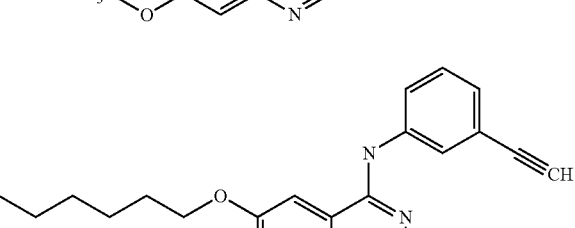 | | | |

TABLE B-continued

| Structure | IC50 (nM) | | |
|---|---|---|---|
| | HDAC | EGFR | HER2/ErbB2 |

[Chemical structure: quinazoline with 4-(4-hydroxy-3-ethynylphenylamino), 6-O-(6-hydroxy-6-oxohexyloxy), 7-OH]

[Chemical structure: quinazoline with 4-(4-hydroxy-3-ethynylphenylamino), 6-O-(6-hydroxy-6-oxo-3-hydroxyhexyloxy chain), 7-OMe]

[Chemical structure: quinazoline with 4-(3-ethynylphenylamino), 6-O-(6-hydroxy-6-oxo-3-hydroxyhexyloxy chain), 7-OMe]

Cell Proliferation Assay:

Cancer cell lines are plated at 5,000 to 10,000 per well in 96-well flatted bottomed plates with various concentration of compounds. The cells are incubated with compounds for 72 hours in the presence of 0.5% of fetal bovine serum. Growth inhibition is accessed by adenosine triphosphate (ATP) content assay using Perkin Elmer ATPlite kit. ATPlite is an ATP monitoring system based on firefly luciferase. Briefly, 25 µl of mammalian cell lysis solution is added to 50 µl of phenol red-free culture medium per well to lyse the cells and stabilize the ATP. 25 µl of substrate solution is then added to the well and subsequently the luminescence is measured.

Tumor cell lines that can be assayed include those listed in TABLES C and D.

TABLE C

| Cell Line |
|---|
| Breast_MCF7 |
| Breast_MDAMB468 |
| Breast_SkBr3 |
| Colon_HCT116 |
| Epidermoid_A431 |
| Lung_H1703 |
| Lung_H1975 |
| Lung_H2122 |
| Lung_H292 |
| Lung_H358 |
| Lung_H460 |
| Lung_HCC827 |
| Pancreas_BxPC3 |
| Pancreas_Capan1 |
| Pancreas_CFPAC |
| Pancreas_HPAC |
| Pancreas_MiaPaCa2 |
| Pancreas_PANC1 |
| Prostate_22RV1 |
| Prostate_PC3 |

TABLE D

| Model | Cancer type |
|---|---|
| A431 | Epidermoid |
| H358 | NSCLC |
| H292 | NSCLC |
| BxPC3 | Pancreatic |
| PC3 | Prostate |
| HCT116 | Colon |
| HCC827 (apoptosis/anti-proliferation) | NSCLC |
| BxPC3 (apoptosis/anti-proliferation) | Pancreatic |

A representative protocol for the in vivo experiment is as followed:

$1\text{-}10\times10^6$ human cancer cells are implanted subcutaneously to the athymic (nu/nu) mice. When the tumors reach about 100 mm$^3$ in volume, the mice are treated with the compound by tail vein infusion. Routinely 5 groups (8-12 mice per group) are needed for a typical efficacy study, including one negative control, one positive control, and three testing groups for 3 dose levels of the same compound. Usually a 7-7-5 (on-off-on) regimen is used for one typical study. The tumor size is measured with an electronic caliper and body weight measured with a scale twice weekly. The tumors are removed from euthanized mice at the end of the study. One half of each tumor is frozen in dry ice and stored at −80° C. for PK or Western blot analysis. The other half is fixed with formalin. The fixed tissues are processed, embedded in paraffin and sectioned for immunohistochemistry staining.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound represented by formula I:

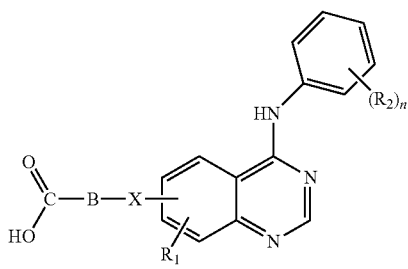

or a pharmaceutically acceptable salt or ester thereof, wherein

X is O, S, CH$_2$, or —CONH—;

B is an unsubstituted C$_5$ to C$_7$ alkylene;

R$_1$ is selected from hydrogen, hydroxy or C$_1$ to C$_4$ alkoxy;

R$_2$ is each independently selected from halogen, hydroxy, C$_1$ to C$_4$ alkyl, C$_2$ to C$_4$ alkenyl, and C$_2$ to C$_4$ alkynyl; and n is 1, 2 or 3.

2. The compound of claim 1 or a pharmaceutically acceptable salt or ester thereof wherein B is an unsubstituted straight chain C$_6$ alkylene.

3. The compound of claim 1 or a pharmaceutically acceptable salt or ester thereof wherein R$_1$ is selected from hydrogen, hydroxy and methoxy.

4. The compound of claim 1 or a pharmaceutically acceptable salt or ester thereof wherein each R$_2$ is independently selected from Br, Cl, F, hydroxy and ethynyl.

5. The compound of claim 1 or a pharmaceutically acceptable salt or ester thereof wherein n is 1 or 2.

6. A pharmaceutical composition comprising as an active ingrdient a compound of claim 1 or a pharmaceutically acceptable salt or ester thereof and a pharmaceutical acceptable carrier.

7. A compound represented by formula (II):

or a pharmaceutically acceptable salt or ester thereof, wherein:

B is an unsubstituted C$_3$ to C$_9$ alkylene;

R$_1$ is selected from hydrogen, hydroxy or C$_1$ to C$_4$ alkoxy;

R2 is each independently selected from halogen, hydroxy, C$_1$ to C$_4$ alkyl, C$_2$ to C$_4$ alkenyl, and C$_2$ to C$_4$ alkenyl; and n is 1, 2 or 3.

8. The compound of claim 7 or a pharmaceutically acceptable salt or ester thereof wherein B is an unsubstituted straight chain C$_5$ to C$_7$ alkylene.

9. The compound of claim 8 or a pharmaceutically acceptable salt or ester thereof wherein B is an unsubstituted straight chain C$_6$ alkylene.

10. A compound according to claim 7 or a pharmaceutically acceptable salt or ester thereof represented by formula (III):

11. The compound of claim 10 or a pharmaceutically acceptable salt or ester thereof wherein B is an unsubstituted straight chain C$_5$ to C$_7$ alkylene.

12. The compound of claim 11 or a pharmaceutically acceptable salt or ester thereof wherein R$_1$ is hydroxy or methoxy and B is an unsubstituted straight chain C$_6$ alkylene.

13. A compound according to claim 7 or a pharmaceutically acceptable salt or ester thereof represented by formula (IV):

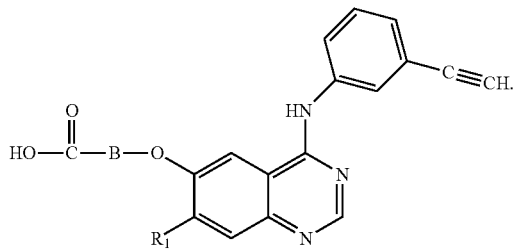

14. The compound of claim 13 or a pharmaceutically acceptable salt or ester thereof wherein B is an unsubstituted straight chain $C_5$ to $C_7$ alkylene.

15. The compound of claim 14 or a pharmaceutically acceptable salt or ester thereof wherein $R_1$ is hydroxy or methoxy and B is an unsubstituted straight chain $C_6$ alkylene.

16. A pharmaceutical composition comprising as an active ingredient a compound of claim 7 or a pharmaceutically acceptable salt or ester thereof and a pharmaceutical acceptable carrier.

17. A compound according to claim 7 or a pharmaceutically acceptable salt or ester thereof represented by formula (V):

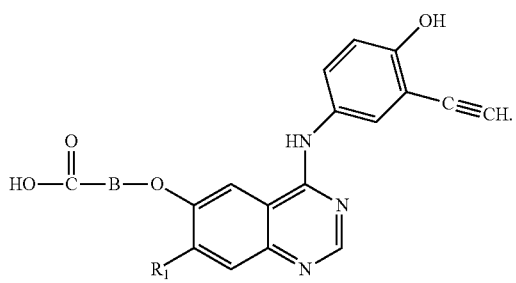

18. The compound of claim 17 or a pharmaceutically acceptable salt or ester thereof wherein B is an unsubstituted straight chain $C_5$ to $C_7$ alkylene.

19. The compound of claim 18 or a pharmaceutically acceptable salt or ester thereof wherein $R_1$ is hydroxy or methoxy and B is an unsubstituted straight chain $C_6$ alkylene.

* * * * *

UNITED STATES PATENT AND TRADEMARK OFFICE
CERTIFICATE OF CORRECTION

PATENT NO. : 8,349,856 B2  
APPLICATION NO. : 13/155788  
DATED : January 8, 2013  
INVENTOR(S) : Changgeng Qian and Xiong Cai Page 1 of 1

It is certified that error appears in the above-identified patent and that said Letters Patent is hereby corrected as shown below:

Column 43  
Claim 6, line 65, please replace "ingrdient" with --ingredient--.

Column 44  
Claim 7, line 25, please replace "C2 to C4 alkenyl;" with --C2 to C4 alkynyl;--.

Signed and Sealed this  
Ninth Day of April, 2013

Teresa Stanek Rea  
*Acting Director of the United States Patent and Trademark Office*